US009687000B2

(12) United States Patent
Bullis et al.

(10) Patent No.: US 9,687,000 B2
(45) Date of Patent: Jun. 27, 2017

(54) PLANT GROWTH-PROMOTING MICROBES AND USES THEREFOR

(71) Applicant: Monsanto Technology LLC, St. Louis, MO (US)

(72) Inventors: David T. Bullis, Cardiff by the Sea, CA (US); Christopher J. Grandlic, San Diego, CA (US); Ryan T. McCann, San Diego, CA (US); Janne S. Kerovuo, San Diego, CA (US)

(73) Assignee: Monsanto Technology LLC, St. Louis, MO (US)

( * ) Notice: Subject to any disclaimer, the term of this patent is extended or adjusted under 35 U.S.C. 154(b) by 20 days.

(21) Appl. No.: 14/362,897

(22) PCT Filed: Dec. 13, 2012

(86) PCT No.: PCT/US2012/069579
§ 371 (c)(1),
(2) Date: Jun. 4, 2014

(87) PCT Pub. No.: WO2013/090628
PCT Pub. Date: Jun. 20, 2013

(65) Prior Publication Data
US 2014/0342905 A1 Nov. 20, 2014

Related U.S. Application Data

(60) Provisional application No. 61/570,237, filed on Dec. 13, 2011.

(51) Int. Cl.
| *C12N 5/04* | (2006.01) |
| *C12N 15/00* | (2006.01) |
| *C12N 15/63* | (2006.01) |
| *C12N 15/82* | (2006.01) |
| *C12N 15/87* | (2006.01) |
| *C12N 5/02* | (2006.01) |
| *C12N 5/10* | (2006.01) |
| *A01N 63/02* | (2006.01) |
| *A01N 63/00* | (2006.01) |
| *C12R 1/07* | (2006.01) |
| *C12N 1/20* | (2006.01) |
| *C12R 1/01* | (2006.01) |
| *C05G 3/02* | (2006.01) |
| *A01H 5/00* | (2006.01) |
| *A01H 1/00* | (2006.01) |
| *A01N 25/08* | (2006.01) |
| *A01N 25/12* | (2006.01) |

(52) U.S. Cl.
CPC ............ *A01N 63/02* (2013.01); *A01N 63/00* (2013.01); *C05G 3/02* (2013.01); *C12N 1/20* (2013.01); *C12R 1/01* (2013.01); *C12R 1/07* (2013.01)

(58) Field of Classification Search
USPC ................ 435/320.1, 419, 430, 468, 252.31; 424/93.4, 93.43, 93.47, 93.46; 504/100
IPC ................ A01H 5/00,1/00; C12N 5/04, 15/00, 15/63, 15/82, 15/87, 5/02, 5/10, 1/20; A01N 25/08, 25/12, 63/00
See application file for complete search history.

(56) References Cited

U.S. PATENT DOCUMENTS

| 4,245,432 | A | 1/1981 | Dannelly |
| 4,339,456 | A | 7/1982 | Rushing |
| 4,372,080 | A | 2/1983 | Rushing |
| 4,465,017 | A | 8/1984 | Simmons |
| 4,634,587 | A | 1/1987 | Hsiao |
| 4,735,015 | A | 4/1988 | Schmolka |
| 4,759,945 | A | 7/1988 | Nemecek et al. |
| 5,328,942 | A | 7/1994 | Akhtar et al. |
| 5,389,399 | A | 2/1995 | Bazin et al. |
| 5,554,445 | A | 9/1996 | Struszczyk et al. |
| 5,580,544 | A | 12/1996 | Dao et al. |
| 5,661,103 | A | 8/1997 | Harms et al. |
| 5,791,084 | A | 8/1998 | Kohno et al. |
| 5,849,320 | A | 12/1998 | Turnblad et al. |
| 5,876,739 | A | 3/1999 | Turnblad et al. |
| 5,918,413 | A | 7/1999 | Otani et al. |
| 5,939,356 | A | 8/1999 | Wellinghoff |
| 6,312,940 | B1 | 11/2001 | Schisler et al. |
| 7,084,331 | B2 | 8/2006 | Isawa et al. |
| 7,097,830 | B2 | 8/2006 | Nautiyal et al. |
| 7,518,040 | B2 | 4/2009 | Komatsuda et al. |

(Continued)

FOREIGN PATENT DOCUMENTS

| EA | 002807 | 10/2002 |
| EP | 1997882 | 12/2008 |

(Continued)

OTHER PUBLICATIONS

Webster et a.l 1997. Interactions of rhizobia with rice and wheat. Plant and Soil, vol. 194, pp. 115-12.2.*

(Continued)

*Primary Examiner* — Debbie K Ware
*Assistant Examiner* — Kailash C Srivastava
(74) *Attorney, Agent, or Firm* — Dentons US LLP; Molly Edwards

(57) ABSTRACT

Microbial strains, compositions, and methods of use thereof to enhance the growth and/or yield of a plant are provided. Also provided are materials and methods for presenting, inhibiting, or treating the development of plant pathogens or phytopathogenic diseases. The disclosure also provides non-naturally occurring plant and derivatives thereof such as plants artificially infected with a microbial strain of the invention.

13 Claims, No Drawings

(56) References Cited

U.S. PATENT DOCUMENTS

| | | | |
|---|---|---|---|
| 7,601,346 | B1 | 10/2009 | Schisler et al. |
| 7,842,494 | B2 | 11/2010 | Kiss et al. |
| 2001/0032343 | A1 | 10/2001 | Hiruma et al. |
| 2003/0172588 | A1 | 9/2003 | Banerjee et al. |
| 2003/0195117 | A1 | 10/2003 | Imada et al. |
| 2003/0211081 | A1* | 11/2003 | da Luz ............... A01N 63/00 424/93.3 |
| 2003/0211119 | A1 | 11/2003 | Nautiyal et al. |
| 2010/0093538 | A1 | 4/2010 | Gnanamanickam |
| 2010/0154299 | A1 | 6/2010 | Kobayashi et al. |
| 2011/0076745 | A1* | 3/2011 | Yuki et al. ............... 435/252.5 |
| 2011/0207604 | A1 | 8/2011 | Asolkar et al. |

FOREIGN PATENT DOCUMENTS

| | | |
|---|---|---|
| JP | 2009/050206 A | 3/2009 |
| KZ | 8751 | 4/2000 |
| KZ | 18025 | 12/2006 |
| RU | 98100477 | 10/1999 |
| SU | 1145503 | 9/1985 |
| WO | WO 2010/109436 | 9/2010 |

OTHER PUBLICATIONS

Rezzonico et al. 2009. Genotypic comparison of Pantoea agglomerans plant and clinical strains. BMC Microbiology vol. 9, p. 204.*
Federal Register / vol. 80, No. 146, Jul. 30, 2015.*
Federal Register /vol. 81, No. 88, May 6, 2016.*
Verma et al. 2001. Evaluation of plant growth promoting and colonization ability of endophytic diazotrophs from deep water rice. Journal of Biotechnology, vol. 91, pp. 127-141.*
Sergeeva et al.,2007 Production of indole-3-acetic acid, aromatic amino acid aminotransferase activities and plant growth promotion by Pantoea agglomerans rhizosphere isolates. Plant Soil, vol. 297, pp. 1-13.*
Feng et al. 2006. Rice endophyte Pantoea agglomerans YS19 promotes host plant growth and affects allocations of host photosynthates. Journal of Applied Bacteriology, vol. 100, pp. 938-945.*
NCBI Gene Accession No. GU459208, dated Jan. 12, 2011.
Mehnaz et al., "Genetic and Phenotypic Diversity of Plant Growth Promoting Rhizobacteria Isolated from Sugarcane Plants Growing in Pakistan," *J. Microbiol. Biotechnol.* 20(12):1614-1623, 2010.
Bakker et al., "Bioassay for studying the role of siderophores in potato growth stimulation by *Pseudomonas* spp. in short potato rotations," *Soil Biology and Biochemistry* 19:443-449, 1987.
Banerjee, "Sulfur-oxidizing bacteria as a potential canola plant growth-promoting Rhizobacteria," *Phytochemicals and Health* 15:330-332, 1995.
Brown, "Seed and Root Bacterization," *Annual Rev. Phytopathology* 68:181-197, 1974.
DeMange et al., "Bacterial siderophores: structure and physicochemical properties of pyoverdines and reiated compounds," *Iron transport in microbes, plants and animals* (Winkleman et al., eds.), pp. 167-176, 1987.
Fall et al., "A simple method to isolate biofilm-forming *Bacillus subtilis* and related species from plant roots," Syst. Appl. Microbiol. 27:372-379, 2004.
Ferreira et al., "Diversity of endpohytic bacteria from *Eucalyptus* species seeds and colonzation of seedlings by Pantoea agglomerans," *FEMS Microbiol. Lett.* 287(1):8-14, 2008.
Gaskins et al,. "Rhizosphere bacteria and their use to increase plant productivity: A review." *Agricult. Ecosyst. Environ.* 12:99-116, 1985.
Gordon et al., "Colorimetric estimation of indoleacetic acid," *Plant Physiol.* 26:192-195, 1951.
Grayston et al., "Sulfur oxidizing bacteria as plant growth promoting rhizobacteria for canola," *Can. J. Microbiol.* 37:521-529, 1991.
Kim et al., "The Multifactorial Basis for Plant Health Promotion by Plant-Associated Bacteria," *Appl. Environ. Microbiol.* 77(5):1548-1555. 2011.
Kloepper et al., "Enhanced plant growth by siderophores produced by plant growth-promoting rhizobacteria," *Nature* 286:885-886, 1980.
Kloepper et al., "*Pseudomonas* siderophores: a mechanism explaining disease-suppressive soils," *Curr. Microbiol.* 4:317-320, 1980.
Myresiotis et al., "Evaluation of plant-growth-promoting rhizobacteria, acibenzolar-S-methyl and hymexazol for integrated control of Fusarium crown and root rot on tomato," *Pest Management Science* 68:404-411, 2011.
Penrose et al., "Methods for isolating and characterizing ACC deaminase-containing plant growth-promoting rhizobacteria," *Physiol. Plant* 118:10-15, 2003.
Ryu et al., "Bacterial volatiles promote growth in Arabidopsis," *Proc. Natl. Acad. Sci.* 100:4927-4932, 2003.
Sudisha et al., "Seed priming with plant gum biopolymers enhances efficacy of metalaxyl 35 SD against pearl millet downy mildew," *Phytoparasitica* 37:161-169, 2009.
Tien et al., "Plant growth substances produced by *Azospinillium brasilense* and their effect on the growth of pearl millet (*Pennisetum americanum* L.)," *Appl. Environ. Microbiol.* 37:1016-1024. 1979.
International Search Report issued in PCT/US2012/069579, dated Mar. 26, 2013.
Supplementary European Search Report regarding Application No. EP 12857082, dated Sep. 28, 2015.
Chernin et al., "Chitinolytic *Enterobacter agglomerans* Antagonistic to Fungal Plant Pathogens," *Applied and Environmental Microbiology* 61(5):1720-1726, 1995.
Wright et al., "*Pantoea agglomerans* Strain EH318 Produces Two Antibiotics That Inhibit *Erwinia amylovora* In Vitro," *Applied and Environmental Microbiology* 67(1):284-292, 2001.
Kazakhstan Office Action regarding Application No. 2014/1640.1, dated Nov. 4, 2015. (English translation).
Morgun et al., "Growth-Stimulating rhizobacteria and their application," *Physiology and Biochemistry of Cultivated Plants* 41(3):187-207, 2009.
GenBank Accession No. EU304255, dated Dec. 24, 2007.
GenBank Accession No. Y17670, dated Mar. 3, 2010.
Son et al., "Solubilization of insoluble inorganic phosphates by a novel salt- and pH-tolerant Pantoea agglomerans R-42 isolated from soybean rhizosphere," *Bioresource Technology* 97:204-210, 2006.

* cited by examiner

PLANT GROWTH-PROMOTING MICROBES AND USES THEREFOR

This application is a 371 National Stage Entry of PCT/US2012/069579, filed Dec. 13, 2012, which claims the benefit of U.S. provisional application 61/570,237, filed Dec. 13, 2011 and each of which are incorporated by reference herein in their entireties including all tables, figures, and claims.

FIELD OF THE INVENTION

The present invention relates to the field of sustainable agriculture. Specifically, the disclosure provides microbial compositions and methods useful for the production of crop plants. In particular, the compositions and methods disclosed herein are useful for enhancing plant growth and/or suppressing the development of plant pathogens and pathogenic diseases.

INCORPORATION OF SEQUENCE LISTING

The material in the accompanying Sequence Listings is hereby incorporated by reference into this application. The accompanying file, named "SGI1540_1WO_CRF_OF_SL_ST25.txt" was created on Dec. 13, 2012 and is 20 KB. The files can be accessed using Microsoft Word on a computer that uses Windows OS.

BACKGROUND OF THE INVENTION

The microflora surrounding plants is very diverse, including bacteria, fungi, yeast, algae. Some of these microorganisms may be deleterious to plants, and are often referred to as pathogens, while others may be beneficial to plants by promoting plant growth and crop productivity. Recent advances in soil microbiology and plant biotechnology have resulted in an increased interest in the use of microbial agents in agriculture, horticulture, forestry and environmental management. In particular, a number of microorganisms known to be present in soil ecological niche, generally known as rhizosphere and rhizoplane, have received considerable attention with respect to their ability to promote plant growth. Indeed, the rhizosphere soil represents a good reservoir of microbes for the potential isolation of beneficial microbes. Plant rhizosphere can contain billions of microorganisms in one gram of soil. In theory, microbial inoculants, without human intervention, have a low survival rate and efficacy in their natural soil environment because of the insufficient colony forming units per gram of soil. Therefore, since the 1960's, a number of biofertilizers that have an increased colony inoculum potential concentration have been developed and commercialized in an attempt to reduce the need for chemical fertilizers.

In addition, research conducted in recent years has shown that microorganisms can be used as biological control agents to increase agricultural productivity and efficiency. These studies have shown that various microorganisms are able to suppress plant pathogens and/or supplement plant growth, thus offering an attractive alternative to chemical pesticides with are less favored because of their potentially negative impact on human health and environment quality.

Microorganisms which can colonize plant roots and stimulate plant growth are generally known as plant growth-promoting microbes (PGPM). In the past two decades, many PGPM species having positive influence on the growth of a wide variety of crop plants have been reported. PGPM are often universal symbionts of higher plants, and are able to enhance the adaptive potential of their hosts through a number of mechanisms, such as the fixation of molecular nitrogen, the mobilization of recalcitrant soil nutrients (e.g., iron, phosphorous, sulfur etc.), the synthesis of phytohormones and vitamins, and the decomposition of plant materials in soils which often increases soil organic matter. Also, certain microbes can facilitate plant growth by controlling microbial species pathogenic to the plant (i.e., phytopathogens). For example, some beneficial microbes can control root rot in plants by competing with fungi for space on the surface of the plant root. In other instances, competition among various microbial strains in a plant's native microflora can stimulate root growth and increase the uptake of mineral nutrients and water to enhance plant yield. Therefore, biofertilizers can be developed as products based on microorganisms that naturally live in the soil. By increasing the population of beneficial microorganisms in the soil through artificial inoculation, these soil microorganisms can boost their biological activity and, thus, supply the plants with important nutrients and beneficial factors that enhance their growth.

The inoculation of cultivated plants with PGPM is generally seen as a promising agricultural approach, for it allows pests to be controlled without using pesticides in large amounts. As environmental concerns about groundwater quality with excess fertilizer and pesticide exposure in foods grow, biological alternatives are becoming necessary. Thus, developing biological treatment compatible with fertilizers and pesticides or even reducing the amount of these chemical compounds could be a significant advancement in the agricultural industry. It has been established that stimulation of plant growth by PGPM is often closely related to the ability of the PGPM to colonize plant roots. However, relatively little attention has been given to the development of efficient selection procedures for obtaining microbial strains with high root-colonizing ability. The lack of such selection procedures slows down the study of plant-bacterial symbioses, and the deployment of PGPM in agriculture.

Therefore, there is a continuing need for the identification of new PGPM and/or testing of their compatibility with existing commercially available crop management products. Moreover, additional investigation is also needed to compare pure culture strains versus complementary mixed strains of microorganisms that form synergistic consortia. Such mixed consortia might have greater potential for consistent performance with better competitive ability under different environmental and growth conditions.

SUMMARY OF THE INVENTION

Microbial strains and cultures are provided herein. Microbial compositions and methods of use thereof to enhance the growth and/or yield of a plant are also provided. Also provided are methods for the treatment of plant seeds by using the microbial compositions disclosed herein. Further provided are methods for preventing, inhibiting, or treating the development of plant pathogens or the development of phytopathogenic diseases. The disclosure also provides non-naturally occurring plant varieties that are varieties artificially infected with a microbial endophyte of the invention. Seed, reproductive tissue, vegetative tissue, regenerative tissues, plant parts, or progeny of the non-naturally occurring plant varieties are also provided. The disclosure further provides a method for preparing agricultural compositions.

In one aspect, the present disclosure provides isolated microbial strains, isolated cultures thereof, biologically pure cultures thereof, and enriched cultures thereof. In certain preferred embodiments of this aspect, the microbial strain can be SGI-003-H11 (deposited as NRRL B-50483); SGI-020-A01 (deposited as NRRL B-50484); SGI-026-G06 (deposited as NRRL B-50485); SGI-026-G07 (deposited as NRRL B-50486), or a strain derived from any one of said strains. In some other preferred embodiments, the microbial strain can comprise a nucleotide or amino acid sequence that exhibits at least 85%, at least 90%, at least 91%, at least 92%, at least 93%, at least 94%, at least 95%, at least 96%, at least 97%, at least 98%, or at least 99% or at least 99.5% sequence identity to any one of the 16S ribosomal and/or recA nucleotide sequences and/or amino acid sequences in the Sequence Listing. In some embodiment the microbial strain also has a plant growth-promoting activity as described herein.

Also provided are microbial compositions that include a microbial strain of the invention or a culture thereof. Such microbial compositions according to some preferred embodiments may comprise an agriculturally effective amount of an additional compound or composition, in which the additional compound or composition may be a fertilizer, an acaricide, a bactericide, a fungicide, an insecticide, a microbicide, a nematicide, or a pesticide. In some other preferred embodiments, the microbial compositions may further include a carrier. In yet other preferred embodiments, the carrier may be a plant seed. In certain embodiments of this aspect, the microbial composition is prepared as a formulation that can be an emulsion, a colloid, a dust, a granule, a pellet, a powder, a spray, an emulsion, or a solution. In some other preferred embodiments, the microbial compositions may be seed coating formulations. In yet another aspect, plant seeds that are coated with a microbial composition in accordance with the present invention are also provided.

In another aspect, there are provided methods for treating plant seeds. Such methods include exposing or contacting the plant seeds with a microbial strain according to the present invention or a culture thereof.

In another aspect of the invention, provided herein are methods for enhancing the growth and/or yield of a plant. In some embodiments, such method involves applying an effective amount of a microbial strain in accordance with the present invention or a culture thereof to the plant, or to the plant's surroundings. In some other embodiments, the method involves growing a microbial strain in accordance with the present invention or a culture thereof in a growth medium or soil of a host plant prior to or concurrent with host plant growth in said growth medium or soil. In preferred embodiments, the plant may be a corn plant or a wheat plant. In some other embodiments, the microbial strain or culture thereof may be established as an endophyte on the plant.

In another aspect of the present invention, there are provided methods for preventing, inhibiting or treating the development of a plant pathogen. Such methods include growing a microbial strain according to the invention or a culture thereof in a growth medium or soil of a host plant prior to or concurrent with host plant growth in said growth medium or soil. In some preferred embodiments, the plant pathogen may be a microorganism of the genus *Colletotrichum, Fusarium, Gibberella, Monographella, Penicillium,* or *Stagnospora*. In some particularly preferred embodiments, the plant pathogen may be *Colletotrichum graminicola, Fusarium graminearum, Gibberella zeae, Monographella nivalis, Penicillium* sp., or *Stagnospora nodurum*.

Another further aspect of the invention provides methods for preventing, inhibiting or treating the development of plant pathogenic disease of a plant. Such methods include applying to the plant, or to the plant's surroundings, an effective amount of a microbial strain according to the invention or a culture thereof. In some preferred embodiments, the microbial strain or a culture thereof may be applied to soil, a seed, a root, a flower, a leaf, a portion of the plant, or the whole plant.

Another further aspect of the invention provides non-naturally occurring plants. The non-naturally occurring plants are artificially infected with a microbial strain of the invention or a culture thereof. Further provided in some embodiments of this aspect are seed, reproductive tissue, vegetative tissue, regenerative tissues, plant parts, and progeny of the non-naturally occurring plants.

Another aspect of the invention provides methods for preparing an agricultural composition. Such methods involve inoculating the microbial strain according to the present invention or a culture thereof into or onto a substratum and allowing it to grow.

In another aspect the invention provides an isolated strain, an isolated culture thereof, a biologically pure culture thereof, and an enriched culture of a microorganism of the genus *Pantoea*. In one embodiment the microorganism comprises a DNA sequence or amino acid sequence coding for a 16S rRNA gene or a recA protein having at least 85%, at least 90%, at least 91%, at least 92%, at least 93%, at least 94%, at least 95%, at least 96%, at least 97%, at least 98%, or at least 99% or at least 99.5% sequence identity to a sequence coding for 16S rRNA gene or recA protein disclosed in the Sequence Listing. In another embodiment the invention provides a genus of microorganisms comprising any of the DNA sequences or amino acid sequences described above and which enhances the growth and/or yield of a plant, as described herein.

These and other objects and features of the invention will become more fully apparent from the following detailed description of the invention and the claims.

DETAILED DESCRIPTION OF THE INVENTION

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

The singular form "a", "an", and "the" include plural references unless the context clearly dictates otherwise. For example, the term "a cell" includes one or more cells, including mixtures thereof.

Bactericidal: the term "bactericidal", as used herein, refers to the ability of a composition or substance to increase mortality or inhibit the growth rate of bacteria.

Biological control: the term "biological control" and its abbreviated form "biocontrol", as used herein, is defined as control of a pathogen or insect or any other undesirable organism by the use of at least a second organism other than man. An example of known mechanisms of biological control is the use of microorganisms that control root rot by out-competing fungi for space on the surface of the root, or microorganisms that either inhibit the growth of or kill the pathogen. The "host plant" in the context of biological control is the plant that is susceptible to disease caused by the pathogen. In the context of isolation of an organism, such as a bacterium or fungal species, from its natural environment, the "host plant" is a plant that supports the growth of the bacterium or fungus, for example, a plant of a species the bacterium or fungus is an endophyte of.

An "effective amount", as used herein, is an amount sufficient to effect beneficial or desired results. An effective amount can be administered in one or more administrations. In terms of treatment, inhibition or protection, an effective amount is that amount sufficient to ameliorate, stabilize, reverse, slow or delay progression of the target infection or disease states. The expression "effective microorganism" used herein in reference to a microorganism is intended to mean that the subject strain exhibits a degree of promotion of plant growth and/or yield or a degree of inhibition of a pathogenic disease that exceeds, at a statistically significant level, that of an untreated control. In some instances, the expression "an effective amount" is used herein in reference to that quantity of microbial treatment which is necessary to obtain a beneficial or desired result relative to that occurring in an untreated control under suitable conditions of treatment as described herein. For the purpose of the present disclosure, the actual rate of application of a liquid formulation will usually vary from a minimum of about $1 \times 10^3$ to about $1 \times 10^{10}$ viable cells/mL and preferably from about $1 \times 10^6$ to about $5 \times 10^9$ viable cells/mL. Under most conditions, the strains of the invention described in the examples below would be optimally effective at application rates in the range of about $1 \times 10^6$ to $1 \times 10^9$ viable cells/mL, assuming a mode of application which would achieve substantially uniform contact of at least about 50% of the plant tissues. If the microorganisms are applied as a solid formulation, the rate of application should be controlled to result in a comparable number of viable cells per unit area of plant tissue surface as obtained by the aforementioned rates of liquid treatment. Typically, the microbial compositions of the present invention are biologically effective when delivered at a concentration in excess of $10^6$ CFU/g (colony forming units per gram), preferably in excess of $10^7$ CFU/g, more preferably $10^8$ CFU/g, and most preferably at $10^9$ CFU/g.

Composition: A "composition" is intended to mean a combination of active agent and at least another compound, carrier, or composition, which can be inert (for example, a detectable agent or label or liquid carrier) or active, such as a fertilizer.

A "control plant", as used in the present disclosure, provides a reference point for measuring changes in phenotype of the subject plant, may be any suitable plant cell, seed, plant component, plant tissue, plant organ or whole plant. A control plant may comprise, for example, (a) a wild-type plant or cell, i.e., of the same genotype as the starting material for the genetic alteration which resulted in the subject plant or cell; (b) a plant or cell of the genotype as the starting material but which has been transformed with a null construct (i.e., a construct which has no known effect on the trait of interest, such as a construct comprising a reporter gene); (c) a plant or cell which is a non-transformed segregant among progeny of a subject plant or cell; (d) a plant or cell which is genetically identical to the subject plant or cell but which is not exposed to the same treatment (e.g., fertilizer treatment) as the subject plant or cell; (e) the subject plant or cell itself, under conditions in which the gene of interest is not expressed; or (f) the subject plant or cell itself, under conditions in which it has not been exposed to a particular treatment such as, for example, a fertilizer or combination of fertilizers and/or other chemicals.

Culture, isolated culture, biologically pure culture, and enriched culture: As used herein, an isolated strain of a microbe is a strain that has been removed from its natural milieu. As such, the term "isolated" does not necessarily reflect the extent to which the microbe has been purified. But in different embodiments an "isolated" culture has been purified at least 2× or 5× or 10× or 50× or 100× from the raw material from which it is isolated. As a non-limiting example, if a culture is isolated from soil as raw material, the organism can be isolated to an extent that its concentration in a given quantity of purified or partially purified material (e.g., soil) is at least 2× or 5× or 10× or 50× or 100× that in the original raw material. A "substantially pure culture" of the strain of microbe refers to a culture which contains substantially no other microbes than the desired strain or strains of microbe. In other words, a substantially pure culture of a strain of microbe is substantially free of other contaminants, which can include microbial contaminants as well as undesirable chemical contaminants. Further, as used herein, a "biologically pure" strain is intended to mean the strain separated from materials with which it is normally associated in nature. Note that a strain associated with other strains, or with compounds or materials that it is not normally found with in nature, is still defined as "biologically pure." A monoculture of a particular strain is, of course, "biologically pure." In different embodiments a "biologically pure" culture has been purified at least 2× or 5× or 10× or 50× or 100× from the material with which it is normally associated in nature. As a non-limiting example, if a culture is normally associated with soil in nature, the organism can be biologically pure to an extent that its concentration in a given quantity of purified or partially purified material with which it is normally associated in nature (e.g. soil) is at least 2× or 5× or 10× or 50× or 100× that in the original unpurified material. As used herein, the term "enriched culture" of an isolated microbial strain refers to a microbial culture wherein the total microbial population of the culture contains more than 50%, 60%, 70%, 80%, 90%, or 95% of the isolated strain.

Culturing: The term 'culturing', as used herein, refers to the propagation of organisms on or in media of various kinds.

As used herein, an "endophyte" is an endosymbiont that lives within a plant for at least part of its life without causing apparent disease. Endophytes may be transmitted either vertically (directly from parent to offspring) or horizontally (from individual to unrelated individual). Vertically-transmitted fungal endophytes are typically asexual and transmit from the maternal plant to offspring via fungal hyphae penetrating the host's seeds. Bacterial endophytes can also be transferred vertically from seeds to seedlings (Ferreira et al., *FEMS Microbiol. Lett.* 287: 8-14, 2008). Conversely, horizontally-transmitted endophytes are typically sexual, and transmit via spores that can be spread by wind and/or insect vectors. Microbial endophytes of crop plants have received considerable attention with respect to their ability to control disease and insect infestation, as well as their potential to promoting plant growth.

Fungal pathogen: For purposes of this invention it is understood that the use of term fungal pathogen or fungus is intended to include both the sexual (teleomorphic) stage of this organism and also the asexual (anamorphic) stage, also referred to as the perfect and imperfect fungal stages, respectively. For example, the anamorphic stage of *Fusarium graminearum* is *Gibberella zeae*.

Fungicidal: As used herein, "fungicidal" refers to the ability of a composition or substance to decrease the rate of growth of fungi or to increase the mortality of fungi.

Mutant: As used herein, the term "mutant" or "variant" in reference to a microorganism refers to a modification of the parental strain in which the desired biological activity is similar to that expressed by the parental strain. For example, in the case of *Burkholderia* the "parental strain" is defined herein as the original *Burkholderia* strain before mutagenesis. Mutants or variants may occur in nature without the intervention of man. They also are obtainable by treatment with or by a variety of methods and compositions known to those of skill in the art. For example, a parental strain may be treated with a chemical such as N-methyl-N'-nitro-N-nitrosoguanidine, ethylmethanesulfone, or by irradiation using gamma, x-ray, or UV-irradiation, or by other means well known to those practiced in the art.

Nematicidal: The term "nematicidal", as used herein, refers to the ability of a substance or composition to increase mortality or inhibit the growth rate of nematodes.

Pathogen: The term "pathogen" as used herein refers to an organism such as an alga, an arachnid, a bacterium, a fungus, an insect, a nematode, a parasitic plant, a protozoan, a yeast, or a virus capable of producing a disease in a plant or animal. The term "phytopathogen" as used herein refers to a pathogenic organism that infects a plant.

Percentage of sequence identity: "percentage of sequence identity", as used herein, is determined by comparing two optimally locally aligned sequences over a comparison window defined by the length of the local alignment between the two sequences. The amino acid sequence in the comparison window may comprise additions or deletions (e.g., gaps or overhangs) as compared to the reference sequence (which does not comprise additions or deletions) for optimal alignment of the two sequences. Local alignment between two sequences only includes segments of each sequence that are deemed to be sufficiently similar according to a criterion that depends on the algorithm used to perform the alignment (e.g. BLAST). The percentage of sequence identity is calculated by determining the number of positions at which the identical nucleic acid base or amino acid residue occurs in both sequences to yield the number of matched positions, dividing the number of matched positions by the total number of positions in the window of comparison and multiplying the result by 100. Optimal alignment of sequences for comparison may be conducted by the local homology algorithm of Smith and Waterman (1981) Add. APL. Math. 2:482, by the global homology alignment algorithm of Needleman and Wunsch (*J Mol. Biol.* 48:443, 1970), by the search for similarity method of Pearson and Lipman (*Proc. Natl. Acad. Sci. USA* 85: 2444, 1988), by heuristic implementations of these algorithms (NCBI BLAST, WU-BLAST, BLAT, SIM, BLASTZ), or by inspection. Given that two sequences have been identified for comparison, GAP and BESTFIT are preferably employed to determine their optimal alignment. Typically, the default values of 5.00 for gap weight and 0.30 for gap weight length are used. The term "substantial sequence identity" between polynucleotide or polypeptide sequences refers to polynucleotide or polypeptide comprising a sequence that has at least 50% sequence identity, preferably at least 70%, preferably at least 80%, more preferably at least 85%, more preferably at least 90%, even more preferably at least 95%, and most preferably at least 96%, 97%, 98% or 99% sequence identity compared to a reference sequence using the programs. In addition, pairwise sequence homology or sequence similarity, as used refers to the percentage of residues that are similar between two sequences aligned. Families of amino acid residues having similar side chains have been well defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Query nucleic acid and amino acid sequences can be searched against subject nucleic acid or amino acid sequences residing in public or proprietary databases. Such searches can be done using the National Center for Biotechnology Information Basic Local Alignment Search Tool (NCBI BLAST v 2.18) program. The NCBI BLAST program is available on the internet from the National Center for Biotechnology Information (blast.ncbi.nlm.nih.gov/Blast.cgi). Typically the following parameters for NCBI BLAST can be used: Filter options set to "default", the Comparison Matrix set to "BLOSUM62", the Gap Costs set to "Existence: 11, Extension: 1", the Word Size set to 3, the Expect (E threshold) set to 1e-3, and the minimum length of the local alignment set to 50% of the query sequence length. Sequence identity and similarity may also be determined using GenomeQuest™ software (Gene-IT, Worcester Mass. USA).

The term "pest" as used herein refers to an undesired organism that may include, but not limited to, bacteria, fungi, plants (e.g., weeds), nematodes, insects, and other pathogenic animals. "Pesticidal", as used herein, refers to the ability of a substance or composition to decrease the rate of growth of a pest, i.e., an undesired organism, or to increase the mortality of a pest.

Progeny: As used herein, "progeny" includes descendants of a particular plant or plant line. Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant.

Variant: as used herein in reference to a nucleic acid and polypeptide, the term "variant" is used herein to denote a polypeptide, protein or polynucleotide molecule with some differences, generated synthetically or naturally, in their amino acid or nucleic acid sequences as compared to a reference polypeptide or polynucleotide, respectively. For example, these differences include substitutions, insertions, deletions or any desired combinations of such changes in a reference polypeptide or polypeptide. Polypeptide and protein variants can further consist of changes in charge and/or post-translational modifications (such as glycosylation, methylation. phosphorylation, etc.)

The term "variant", when used herein in reference to a microorganism, is a microbial strain having identifying characteristics of the species to which it belongs, while having at least one nucleotide sequence variation or identifiably different trait with respect to the parental strain, where the trait is genetically based (heritable). For example, for a

*Bacillus thuringiensis* 020_A01 strain having a plant growth-promoting activity, identifiable traits include 1) the ability to suppress the development of fungal phytopathogens, including *Fusarium graminearum, Gibberella zeae, Stagnospora nodurum, Colletotrichum graminicola;* 2) the ability to enhance seed yield in wheat; and 3) having a 16S rRNA gene with nucleotide sequence with greater than 95%, greater than 96%, greater than 97%, greater than 98%, or greater than 99% sequence identity to the 16S rRNA gene of *Bacillus thuringiensis* 020_A01; can be used to confirm a variant as *Bacillus thuringiensis* 020_A01.

Yield: As used herein, the term "yield" refers to the amount of harvestable plant material or plant-derived product, and is normally defined as the measurable produce of economic value of a crop. For crop plants, "yield" also means the amount of harvested material per acre or unit of production. Yield may be defined in terms of quantity or quality. The harvested material may vary from crop to crop, for example, it may be seeds, above ground biomass, roots, fruits, cotton fibers, any other part of the plant, or any plant-derived product which is of economic value. The term "yield" also encompasses yield potential, which is the maximum obtainable yield. Yield may be dependent on a number of yield components, which may be monitored by certain parameters. These parameters are well known to persons skilled in the art and vary from crop to crop. The term "yield" also encompasses harvest index, which is the ratio between the harvested biomass over the total amount of biomass.

All publications and patent applications mentioned in this specification are herein incorporated by reference to the same extent as if each individual publication or patent application was specifically and individually indicated to be incorporated by reference.

No admission is made that any reference constitutes prior art. The discussion of the references states what their authors assert, and the applicants reserve the right to challenge the accuracy and pertinence of the cited documents. It will be clearly understood that, although a number of prior art publications are referred to herein, this reference does not constitute an admission that any of these documents forms part of the common general knowledge in the art.

The discussion of the general methods given herein is intended for illustrative purposes only. Other alternative methods and embodiments will be apparent to those of skill in the art upon review of this disclosure.

Plant Growth-Promoting Microorganisms

Diverse plant-associated microorganisms can positively impact plant health and physiology in a variety of ways. These beneficial microbes are generally referred to as plant growth-promoting microorganisms (PGPMs). The term "plant growth-promoting activity", as used herein, encompasses a wide range of improved plant properties, including, for example without limitation, improved nitrogen fixation, improved root development, increased leaf area, increased plant yield, increased seed germination, increased photosynthesis, or an increased in accumulated biomass of the plant. In various embodiments the improvement is an at least 10% increase or at least 25% increase or at least 50% increase or at least 75% increase or at least a 100% increase in the property being measured. Thus, as non-limiting examples, the microbes may produce an above stated percentage increase in nitrogen fixation, or an above stated increase in total root weight, or in leaf area or in plant product yield (e.g., an above stated percentage increase in plant product weight), or an increased percentage of seeds that germinate within 10 days or 14 days or 30 days, or rate of photosynthesis (e.g., determined by $CO_2$ consumption) or accumulated biomass of the plant (e.g., determined by weight of the plant). The plant product is the item—usually but not necessarily—a food item produced by the plant. The yield can be determined using any convenient method, for example, bushels or pounds of plant product produced per acre of planting. To date, isolated strains of over two dozen genera of microorganisms have been reported to have plant growth-promoting activity and/or biocontrol activity, and new genera and species with similar activities are still being discovered. Additionally, within some bacterial genera, multiple species and subspecies of biocontrol agents have been identified and can be found across multiple spatial scales, from the global level to farm level, and even on single plants. Furthermore, it has been reported that some individual microbial isolates may display biocontrol and/or plant growth-promoting activity not only on the plants or crops from which they were obtained but also on other crops. This indicates the generalist nature of some genotypes, especially those with a wide geographic distribution. As discussed above, if introduced in sufficient numbers and active for a sufficient duration, a single microbial population can have a significant impact on plant health.

Several mechanisms have been postulated to provide an explanation for the positive impact of PGPMs on plant growth enhancement. The beneficial effects of the microorganisms on plant growth can be direct or indirect.

The term "direct plant growth-promoting microorganism", for the purpose of this disclosure, refers to a microorganism that can enhance plant growth in the absence of pathogens. As discussed in more detail below, examples of direct plant growth promotion include (a) biofertilization, (b) stimulation of root growth, (c) rhizoremediation, and (d) plant stress control. In addition, several PGPMs have been reported to promote plant growth indirectly via mechanisms of biological control, i.e., by reducing the level of disease, for example antibiosis, induction of systemic resistance, and competition with pathogens for nutrients and niches.

Biofertilizers: Microbial fertilizers supply the plant with nutrients and thereby can promote plant growth in the absence of pathogen pressure. Non-limiting examples of microbial isolates that can directly promote plant growth and/yield include $N_2$-fixing bacteria *Rhizobium* and *Bradyrhizobium* species that, through symbiotic nitrogen fixation, can form nodules on roots of leguminous plants, in which they convert atmospheric $N_2$ into ammonia which, in contrast to atmospheric $N_2$, can be used by the plant as a nitrogen source. Other examples include *Azospirillum* species, which are free-living $N_2$-fixers that can fertilize and increase yield of cereal crops such as wheat, *sorghum*, and maize. Despite *Azospirillum*'s $N_2$-fixing capacity, the yield increase caused by inoculation by *Azospirillum* is often attributed to increased root development and thus to increased rates of water and mineral uptake. In this respect, several rhizobacteria like *Azotobacter* spp. have been reported to be capable of producing a wide array of phytohormones (e.g., auxins, cytokinins) and enzymes (e.g., pectinase). Many of these phytohormones and enzymes have been shown to be intimately involved in the infection process of symbiotic bacteria-plant associations which have a regulatory influence on nodulation by *Rhizobium*.

In many instances, PGPMs also can affect the plant growth and development by modifying nutrient uptake. They may alter nutrient uptake rates, for example, by direct effects on roots, by effects on the environment which in turn modify root behavior, and by competing directly for nutrients (Gaskin et al., *Agricult. Ecosyst. Environ.* 12: 99-116, 1985). Some factors by which PGPM may play a role in modifying the nutrient use efficiency in soils include, for example, root geometry, nutrient solubility, nutrient availability by producing plant congenial ion form, partitioning of the nutrients in plant and utilization efficiency. For example, a low level of soluble phosphate can limit the growth of plants. Some plant growth-promoting microbes are capable of solubilizing phosphate from either organic or inorganic bound phosphates, thereby facilitating plant growth. Several enzymes of microbial origin, such as non-specific phosphatases, phytases, phosphonatases, and C-P lyases, release soluble phosphorus from organic compounds in soil. For example, an increased solubilization of inorganic phosphorous in soil has been found to enhance phosphorus uptake in canola seedling using *Pseudomonas putida* as well as increased sulfur-oxidation and sulfur uptake (Grayston and Germida, *Can. J. Microbiol.* 37: 521-529, 1991; Banerjee, *Phytochemicals and Health*, vol. 15, May 18, 1995).

Phytostimulators: Some microorganisms can produce substances that stimulate the growth of plant in the absence of pathogens. For example, the production of plant hormones is a characteristic of many plant-associated microorganisms. For all five classical phytohormones, i.e., auxin, ethylene, abscisic acid, cytokinin, and gibberellin, synthesis as a secondary metabolite has been demonstrated for at least one bacterial and/or fungal species (for review, see, e.g., Kim et al., *Appl. Environ. Microbiol.*, Vol. 77, 5:1548-1555, 2011). Some microorganisms can also produce secondary metabolites that affect phytohormone production in plants. Probably, the best-known example is hormone auxin, which can promote root growth. Other examples include pseudomonads which have been reported to produce indole acetic acid (IAA) and to enhance the amounts of IAA in plants, thus having a profound impact on plant biomass production (Brown, *Annual Rev. Phytopathology*, 68: 181-197, 1974). For example, Tien et al. (*Applied Environmental Microbiol.*, 37:1016-1024, 1979) reported that inoculation of nutrient solutions around roots of pearl millet with *Azospirillum brasiliense* resulted in increased shoot and root weight, an increased number of lateral roots, and all lateral roots were densely covered with root hairs. Plants supplied with combinations of IAA, gibberellins and kinetin showed an increase in the production of lateral roots similar to that caused by *Azospirilla*. Although the biological significance of these phytohormones and plant-hormone-like materials are not fully understood, the growth stimulating activity of these microorganisms is commonly attributed to their production of these materials.

In addition, other hormones as well as certain volatile organic compounds (VOCs) and the cofactor pyrrolquinoline quinone (PQQ) also stimulate plant growth. For example, some rhizobacteria, such as strains of the bacterial species *B. subtilis, B. amyloliquefaciens*, and *Enterobacter cloacae*, promote plant growth by releasing VOCs. The highest level of growth promotion has been observed with 2,3-butanediol and 3-hydroxy-2-butanone (also referred to as acetoin) as elicitors of induced systemic resistance. The cofactor PQQ has been described as a plant growth promoter, which acts as an antioxidant in plants. Some reports suggests that effect may be indirect because PQQ is a cofactor of several enzymes, e.g., involved in antifungal activity and induction of systemic resistance.

Stress controllers: Plant growth-promoting microorganisms that contain the enzyme 1-aminocyclopropane-1-carboxylic acid (ACC) deaminase facilitate plant growth and development by decreasing plant ethylene levels. Such microorganisms take up the ethylene precursor ACC and convert it into 2-oxobutanoate and $NH_3$. Several types of stress have been reported to be relieved by ACC deaminase producers, such as, for example, stress from the effects of phytopathogenic bacteria, stress from polyaromatic hydrocarbons, stress from heavy metal such as $Ca^{2+}$ and $Ni^{2+}$, and stress from salt and drought.

In addition, several PGPM strains that induced yield increases of potato have been reported to produce extracellular siderophores that bind $Fe^{3+}$, making it less available to certain member of natural microflora (Kloepper et al., *Nature* 286: 885-886, 1980). These rhizobacteria excrete low molecular weight, high affinity ferric-chelating microbial cofactors that specifically enhance their acquisition of iron by binding to membrane bound siderophore receptors. One of the siderophores produced by some pseudomonad PGPMs is known as pseudobactin that inhibits the growth of *Erwinia cartovora* (causal organism for soft-rot of potato) (see, e.g., Kloepper et al., *Current Microbiol.* 4: 317-320, 1980). Additions of pseudobactin to the growth medium inhibited soft-rot infection and also reduced the number of pathogenic fungi in the potato plant along with a significant increase in potato yield. Most evidence to support the siderophore theory of biological control by PGPM comes from work with the pyoverdines, one class of sideophores that comprises the fluorescent pigments of fluorescent pseudomonads [Demange et al., in *Iron Transport in Microbes, Plants and Animals* (Winkleman et al., eds.), pp 167-187, 1987]. According to the siderophore theory, pyoverdines demonstrate certain functional strain specificity which is due to selective recognition of outer membrane siderophore receptors (Bakker et al., *Soil Biology and Biochemistry* 19: 443-450, 1989).

Isolated Cultures of the Invention

As described in more detail in the Examples section of the present disclosure, Applicants have discovered several novel microorganisms that are effective promoters of plant growth and plant yield. In many cases, the isolated microorganisms are also effective in suppressing the development of several plant pathogenic diseases. The microbial isolates were selected from a pool of approximately 5,000 microbial strains obtained from environmental samples collected from several locations throughout the United States. Initial selection of the microorganisms was based on the ability of the microorganisms to colonize plant roots and to produce chemical compounds and enzymes that are considered to be important for their interaction with plants. The microorganisms were also bio-assayed for their ability to suppress the development of various fungal phytopathogens in an in vitro antagonism assay. Selected microbial microorganisms were then bio-assayed in greenhouse studies on commercial wheat and corn varieties for the ability of the microbial strains to promote plant growth and for their ability to preserve seed yield potential.

Taxonomic analysis further determined that representative microorganisms described in the present disclosure are closely related to the bacterial genera *Bacillus, Burkholderia, Herbaspirillum, Pantoea*, and *Pedobacter.*

Deposit of Biological Material

Purified cultures of microbial strains described in the present disclosure were deposited in the Agricultural Research Service Culture Collection located at 1815 N. University Street, Peoria, Ill. 61604, USA (NRRL) in accordance with the Budapest Treaty for the purpose of patent procedure and the regulations thereunder (Budapest Treaty). Accession numbers for these deposits are as follows:

TABLE 1

| Microbial isolates and corresponding accession numbers | | |
|---|---|---|
| Strain ID | Accession Number | Provisional Taxonomy |
| SGI-003-H11 | NRRL B-50483 | *Pantoea agglomerans* 003_H11 |
| SGI-020-A01 | NRRL B-50484 | *Bacillus thuringiensis* 020_A01 |
| SGI-026-G06 | NRRL B-50485 | *Burkholderia metallica* 026_G06 |
| SGI-026-G07 | NRRL B-50486 | *Burkholderia vietnamiensis* 026_G07 |

The microbial strains have been deposited under conditions that ensure that access to the culture will be available during the pendency of this patent application to one determined by the Commissioner of Patents and Trademarks to be entitled thereto under 37 C.F.R. §1.14 and 35 U.S.C. §122. The deposits represent substantially pure cultures of the deposited strains. The deposits are available as required by foreign patent laws in countries wherein counterparts of the subject application or its progeny are filed. However, it should be understood that the availability of a deposit does not constitute a license to practice the subject invention in derogation of patent rights granted by governmental action.

Preferred microorganisms of the present invention have all of the identifying characteristics of the deposited strains and, in particular, the identifying characteristics of being able to promote plant growth and/or yield as described herein, and the identifying characteristics as being able to suppress the development of fungal phytopathogen as described herein. In particular, the preferred microorganisms of the present invention refer to the deposited microorganisms as described above, and strains derived therefrom.

Microbiological Compositions

The microbiological compositions of the present invention that comprise isolated microbial strains or cultures thereof can be in a variety of forms, including, but not limited to, still cultures, whole cultures, stored stocks of cells, mycelium and/or hyphae (particularly glycerol stocks), agar strips, stored agar plugs in glycerol/water, freeze dried stocks, and dried stocks such as lyophilisate or mycelia dried onto filter paper or grain seeds. As defined elsewhere herein, "isolated culture" or grammatical equivalents as used in this disclosure and in the art is understood to mean that the referred to culture is a culture fluid, pellet, scraping, dried sample, lyophilisate, or section (for example, hyphae or mycelia); or a support, container, or medium such as a plate, paper, filter, matrix, straw, pipette or pipette tip, fiber, needle, gel, swab, tube, vial, particle, etc. that contains a single type of organism. In the present invention, an isolated culture of a microbial antagonist is a culture fluid or a scraping, pellet, dried preparation, lyophilisate, or section of the microorganism, or a support, container, or medium that contains the microorganism, in the absence of other organisms.

The present disclosure further provides compositions that contain at least one isolated microbial strains or cultures thereof of the present invention and a carrier. The carrier may be any one or more of a number of carriers that confer a variety of properties, such as increased stability, wettability, dispersability, etc. Wetting agents such as natural or synthetic surfactants, which can be nonionic or ionic surfactants, or a combination thereof can be included in a composition of the invention. Water-in-oil emulsions can also be used to formulate a composition that includes at least one isolated microorganism of the present invention (see, for example, U.S. Pat. No. 7,485,451, incorporated by reference herein). Suitable formulations that may be prepared include wettable powders, granules, gels, agar strips or pellets, thickeners, and the like, microencapsulated particles, and the like, liquids such as aqueous flowables, aqueous suspensions, water-in-oil emulsions, etc. The formulation may include grain or legume products (e.g., ground grain or beans, broth or flour derived from grain or beans), starch, sugar, or oil. The carrier may be an agricultural carrier. In certain preferred embodiments, the carrier is a seed, and the composition may be applied or coated onto the seed or allowed to saturate the seed.

In some embodiments, the agricultural carrier may be soil or plant growth medium. Other agricultural carriers that may be used include water, fertilizers, plant-based oils, humectants, or combinations thereof. Alternatively, the agricultural carrier may be a solid, such as diatomaceous earth, loam, silica, alginate, clay, bentonite, vermiculite, seed cases, other plant and animal products, or combinations, including granules, pellets, or suspensions. Mixtures of any of the aforementioned ingredients are also contemplated as carriers, such as but not limited to, pesta (flour and kaolin clay), agar or flour-based pellets in loam, sand, or clay, etc. Formulations may include food sources for the cultured organisms, such as barley, rice, or other biological materials such as seed, plant parts, sugar cane bagasse, hulls or stalks from grain processing, ground plant material ("yard waste") or wood from building site refuse, sawdust or small fibers from recycling of paper, fabric, or wood. Other suitable formulations will be known to those skilled in the art.

In the liquid form, e.g., solutions or suspensions, the microorganisms of the present invention may be mixed or suspended in water or in aqueous solutions. Suitable liquid diluents or carriers include water, aqueous solutions, petroleum distillates, or other liquid carriers.

Solid compositions can be prepared by dispersing the microorganisms of the invention in and on an appropriately divided solid carrier, such as peat, wheat, bran, vermiculite, clay, talc, bentonite, diatomaceous earth, fuller's earth, pasteurized soil, and the like. When such formulations are used as wettable powders, biologically compatible dispersing agents such as non-ionic, anionic, amphoteric, or cationic dispersing and emulsifying agents can be used.

In a preferred embodiment, the compositions contemplated herein enhance the growth and yield of crop plants, such as wheat, barley, oat, and corn and, when used in sufficient amounts, to act as microbial fertilizer. These compositions, similarly to other biofertilizer agents, can have a high margin of safety because they typically do not burn or injury the plant.

As described in great detail throughout the present disclosure, enhancing plant growth and plant yield may be effected by application of one or more of the microbiological compositions of the present invention to a host plant or parts of the host plant. The compositions can be applied in an amount effective to enhance plant growth or yield relative to that in an untreated control. The active constituents are used in a concentration sufficient to enhance the growth of the target plant when applied to the plant. As will be apparent to a skilled person in the art, effective concentrations may vary depending upon various factors such as, for example, (a) the type of the plant or agricultural commodity; (b) the physiological condition of the plant or agricultural commodity; (c) the concentration of pathogens affecting the plant or agricultural commodity; (d) the type of disease injury on the plant or agricultural commodity; (e) weather conditions (e.g., temperature, humidity); and (f) the stage of plant disease. According to the present invention, typical concentrations are those higher than $1\times10^2$ CFU/mL of carrier. Preferred concentrations range from about $1\times10^4$ to about $1 \times 10^9$ CFU/mL, such as the concentrations ranging from $1 \times 10^6$ to $1 \times 10^8$ CFU/mL. More preferred concentrations are those of from about 37.5 to about 150 mg dry bacterial mass per milliliter of carrier (liquid composition) or per gram of carrier (dry formulation).

In some embodiments, the amount of one or more of the microorganisms in the compositions of the present invention can vary depending on the final formulation as well as size or type of the plant or seed utilized. Preferably, the one or more microorganisms in the compositions are present in about 2% w/w/ to about 80% w/w of the entire formulation. More preferable, the one or more microorganisms employed in the compositions is about 5% w/w to about 65% w/w and most preferably about 10% w/w to about 60% w/w by weight of the entire formulation.

As it will be appreciated by those skilled in the art, the microbiological compositions of the invention may be applied to the target plant using a variety of conventional methods such as dusting, coating, injecting, rubbing, rolling, dipping, spraying, or brushing, or any other appropriate technique which does not significantly injure the target plant to be treated. Particularly preferred methods include the inoculation of growth medium or soil with suspensions of microbial cells and the coating of plant seeds with microbial cells and/or spores.

Typically, the compositions of the invention are chemically inert; hence they are compatible with substantially any other constituents of the application schedule. They may also be used in combination with plant growth affecting substances, such as fertilizers, plant growth regulators, and the like, provided that such compounds or substances are biologically compatible. They can also be used in combination with biologically compatible pesticidal active agents as for example, herbicides, nematocides, fungicides, insecticides, and the like.

When used as biofertilizers in their commercially available formulations and in the use forms, prepared from these formulations, the active microbial strains and compositions according to the present invention can furthermore be present in the form of a mixture with synergists. Synergists are compounds by which the activity of the active compositions is increased without it being necessary for the synergist added to be active itself.

When used as biofertilizers in their commercially available formulations and in the use forms, prepared from these formulations, the active microbial strains and compositions according to the invention can furthermore be present in the form of a mixture with inhibitors which reduce the degradation of the active compositions after application in the habitat of the plant, on the surface of parts of plants or in plant tissues.

The active microbial strains and compositions according to the invention, as such or in their formulations, can also be used as a mixture with known fertilizers, acaricides, bactericides, fungicides, insecticides, microbicides, nematicides, pesticides, or combinations of any thereof, for example in order to widen the spectrum of action or to prevent the development of resistances to pesticides in this way. In many cases, synergistic effects result, i.e., the activity of the mixture can exceed the activity of the individual components. A mixture with other known active compounds, such as growth regulators, safeners and/or semiochemicals is also contemplated.

In a preferred embodiment of the present invention, the compositions may further include at least one chemical or biological fertilizer. The amount of at least one chemical or biological fertilizer employed in the compositions can vary depending on the final formulation as well as the size of the plant and seed to be treated. Preferably, the at least one chemical or biological fertilizer employed is about 0.1% w/w to about 80% w/w based on the entire formulation. More preferably, the at least one chemical or biological fertilizer is present in an amount of about 1% w/w to about 60% w/w and most preferably about 10% w/w to about 50% w/w.

The microbiological compositions of the present invention preferably include at least one biological fertilizer. Exemplary biological fertilizers that are suitable for use herein and can be included in a microbiological composition according to the present invention for promoting plant growth and/yield include microbes, animals, bacteria, fungi, genetic material, plant, and natural products of living organisms. In these compositions, the microorganism of the present invention is isolated prior to formulation with an additional organism. For example, microbes such as but not limited to species of *Achromobacter, Ampelomyces, Aureobasidium, Azospirillum, Azotobacter, Bacillus, Beauveria, Bradyrhizobium, Candida, Chaetomium, Cordyceps, Cryptococcus, Dabaryomyces, Delftia, Erwinia, Exophilia, Gliocladium, Herbaspirillum, Lactobacillus, Mariannaea, Microccocus, Paecilomyces, Paenibacillus, Pantoea, Pichia, Pseudomonas, Rhizobium, Saccharomyces, Sporobolomyces, Stenotrophomonas, Streptomyces, Talaromyces*, and *Trichoderma* can be provided in a composition with the microorganisms of the present invention. Use of the microbiological compositions according to the present invention in combination with the microbial microorganisms disclosed in U.S. Patent Appl. Nos. US20030172588A1, US20030211119A1; U.S. Pat. Nos. 7,084,331; 7,097,830; 7,842,494; PCT Appl. No. WO2010109436A1 is also particularly preferred.

In a preferred embodiment of the present invention, the compositions may further include at least one chemical or biological pesticide. The amount of at least one chemical or biological pesticide employed in the compositions can vary depending on the final formulation as well as the size of the plant and seed to be treated. Preferably, the at least one chemical or biological pesticide employed is about 0.1% w/w to about 80% w/w based on the entire formulation. More preferably, the at least one chemical or biological pesticide is present in an amount of about 1% w/w to about 60% w/w and most preferably about 10% w/w to about 50% w/w.

A variety of chemical pesticides is apparent to one of skill in the art and may be used. Exemplary chemical pesticides include those in the carbamate, organophosphate, organochlorine, and prethroid classes. Also included are chemical control agents such as, but not limited to, benomyl, borax, captafol, captan, chorothalonil, formulations containing copper; formulations containing dichlone, dicloran, iodine, zinc; fungicides that inhibit ergosterol biosynthesis such as but not limited to blastididin, cymoxanil, fenarimol, flusilazole, folpet, imazalil, ipordione, maneb, manocozeb, metalaxyl, oxycarboxin, myclobutanil, oxytetracycline, PCNB, pentachlorophenol, prochloraz, propiconazole, quinomethionate, sodium aresenite, sodium DNOC, sodium hypochlorite, sodium phenylphenate, streptomycin, sulfur, tebuconazole, terbutrazole, thiabendazolel, thiophanate-methyl, triadimefon, tricyclazole, triforine, validimycin, vinclozolin, zineb, and ziram.

The microbiological compositions of the present invention preferably include at least one biological pesticide. Exemplary biological pesticides that are suitable for use herein and can be included in a microbiological composition according to the present invention for preventing a plant pathogenic disease include microbes, animals, bacteria, fungi, genetic material, plant, and natural products of living organisms. In these compositions, the microorganism of the present invention is isolated prior to formulation with an additional organism. For example, microbes such as but not limited to species of *Ampelomyces, Aureobasidium, Bacillus, Beauveria, Candida, Chaetomium, Cordyceps, Cryptococcus, Dabaryomyces, Erwinia, Exophilia, Gliocladium, Mariannaea, Paecilomyces, Paenibacillus, Pantoea, Pichia, Pseudomonas, Sporobolomyces, Talaromyces*, and *Trichoderma* can be provided in a composition with the microorganisms of the present invention, with fungal strains of the *Muscodor* genus being particularly preferred. Use of the microbiological compositions according to the present invention in combination with the microbial antagonists disclosed in U.S. Pat. No. 7,518,040; U.S. Pat. No. 7,601,346; U.S. Pat. No. 6,312,940 is also particularly preferred.

Examples of fungi that can be combined with microbial strains and compositions of the present invention in a composition include, without limitation, *Muscodor* species, *Aschersonia aleyrodis, Beauveria bassiana* ("white muscarine"), *Beauveria brongniartii, Chladosporium herbarum, Cordyceps clavulata, Cordyceps entomorrhiza, Cordyceps facis, Cordyceps gracilis, Cordyceps melolanthae, Cordyceps militaris, Cordyceps myrmecophila, Cordyceps ravenelii, Cordyceps sinensis, Cordyceps sphecocephala, Cordyceps subsessilis, Cordyceps unilateralis, Cordyceps variabilis, Cordyceps washingtonensis, Culicinomyces clavosporus, Entomophaga grylli, Entomophaga maimaiga, Entomophaga muscae, Entomophaga praxibulli, Entomophthora plutellae, Fusarium lateritium, Hirsutella citriformis, Hirsutella thompsoni, Metarhizium anisopliae* ("green muscarine"), *Metarhizium flaviride, Muscodor albus, Neozygitesfloridana, Nomuraea rileyi, Paecilomyces farinosus, Paecilomyces fumosoroseus, Pandora neoaphidis, Tolypocladium cylindrosporum, Verticillium lecanii, Zoophthora radicans*, and mycorrhizal species such as *Laccaria bicolor*. Other mycopesticidal species will be apparent to those skilled in the art.

The present invention also provides methods of treating a plant by application of any of a variety of customary formulations in an effective amount to either the soil (i.e., in-furrow), a portion of the plant (i.e., drench) or on the seed before planting (i.e., seed coating or dressing). Customary formulations include solutions, emulsifiable concentrate, wettable powders, suspension concentrate, soluble powders, granules, suspension-emulsion concentrate, natural and synthetic materials impregnated with active compound, and very fine control release capsules in polymeric substances. In certain embodiments of the present invention, the microbial compositions are formulated in powders that are available in either a ready-to-use formulation or are mixed together at the time of use. In either embodiment, the powder may be admixed with the soil prior to or at the time of planting. In an alternative embodiment, one or both of either the plant growth-promoting agent or biocontrol agent is a liquid formulation that is mixed together at the time of treating. One of ordinary skill in the art understands that an effective amount of the inventive compositions depends on the final formulation of the composition as well as the size of the plant or the size of the seed to be treated.

Depending on the final formulation and method of application, one or more suitable additives can also be introduced to the compositions of the present invention. Adhesives such as carboxymethylcellulose and natural and synthetic polymers in the form of powders, granules or latexes, such as gum arabic, chitin, polyvinyl alcohol and polyvinyl acetate, as well as natural phospholipids, such as cephalins and lecithins, and synthetic phospholipids, can be added to the present compositions.

In a preferred embodiment, the microbiological compositions are formulated in a single, stable solution, or emulsion, or suspension. For solutions, the active chemical compounds are typically dissolved in solvents before the biological agent is added. Suitable liquid solvents include petroleum based aromatics, such as xylene, toluene or alkylnaphthalenes, aliphatic hydrocarbons, such as cyclohexane or paraffins, for example petroleum fractions, mineral and vegetable oils, alcohols, such as butanol or glycol as well as their ethers and esters, ketones, such as methyl ethyl ketone, methyl isobutyl ketone or cyclohexanone, strongly polar solvents, such as dimethylformamide and dimethyl sulphoxide. For emulsion or suspension, the liquid medium is water. In one embodiment, the chemical agent and biological agent are suspended in separate liquids and mixed at the time of application. In a preferred embodiment of suspension, the chemical agent and biological agent are combined in a ready-to-use formulation that exhibits a reasonably long shelf-life. In use, the liquid can be sprayed or can be applied foliarly as an atomized spray or in-furrow at the time of planting the crop. The liquid composition can be introduced in an effective amount on the seed (i.e., seed coating or dressing) or to the soil (i.e., in-furrow) before germination of the seed or directly to the soil in contact with the roots by utilizing a variety of techniques known in the art including, but not limited to, drip irrigation, sprinklers, soil injection or soil drenching.

Optionally, stabilizers and buffers can be added, including alkaline and alkaline earth metal salts and organic acids, such as citric acid and ascorbic acid, inorganic acids, such as hydrochloric acid or sulfuric acid. Biocides can also be added and can include formaldehydes or formaldehyde-releasing agents and derivatives of benzoic acid, such as p-hydroxybenzoic acid.

Pathogens

The skilled artisan in the art will recognize that the methods and compositions according to the present invention in principle can be applied to suppress the development of any plant pathogens or any phytopathogenic diseases. It is not intended that the invention be limited to a particular culture types or cell types. For example, microbial cells that undergo complex forms of differentiation, filamentation, sporulation, etc. can also be used for the methods and compositions of the present invention.

Examples of phytopathogenic diseases that are suitable for applications of the methods and materials of the present inventions include, but are not limited to, diseases caused by a broad range of pathogenic fungi. The methods of the present invention are preferably applied against pathogenic fungi that are important or interesting for agriculture, horticulture, plant biomass for the production of biofuel molecules and other chemicals, and/or forestry. Of particular interest are pathogenic *Pseudomonas* species (e.g., *Pseudomonas solanacearum*), *Xylella fastidiosa; Ralstonia solanacearum, Xanthomonas campestris, Erwinia amylovora, Fusarium* species, *Phytophthora* species (e.g., *P. infestans*), *Botrytis* species, *Leptosphaeria* species, powdery mildews (Ascomycota) and rusts (Basidiomycota), etc.

Non-limiting examples of plant pathogens of interest include, for instance, *Acremonium strictum, Agrobacterium tumefaciens, Alternaria alternate, Alternaria solani, Aphanomyces euteiches, Aspergillus fumigatus, Athelia rolfsii, Aureobasidium pullulans, Bipolaris zeicola, Botrytis* cinerea, Calonectria kyotensis, Cephalosporium maydis, Cercospora medicaginis, Cercospora sojina, Colletotrichum coccodes, Colletotrichum fragariae, Colletotrichum graminicola, Coniella diplodiella, Coprinopsis psychromorbida, Corynespora cassiicola, Curvularia pallescens, Cylindrocladium crotalariae, Diplocarpon earlianum, Diplodia gossyina, Diplodia spp., Epicoccum nigrum, Erysiphe cichoracearum, Fusarium graminearum, Fusarium oxysporum, Fusarium oxysporum fsp. tuberosi, Fusarium proliferatum var. proliferatum, Fusarium solani, Fusarium verticillioides, Ganoderma boninense, Geotrichum candidum, Glomerella tucumanensis, Guignardia bidwellii, Kabatiella zeae, Leptosphaerulina briosiana, Leptotrochila medicaginis, Macrophomina, Macrophomina phaseolina, Magnaporthe grisea, Magnaporthe oryzae, Microsphaera manshurica, Monilinia fructicola, Mycosphaerella fijiensis, Mycosphaerella fragariae, Nigrospora oryzae, Ophiostoma ulmi, Pectobacterium carotovorum, Pellicularia sasakii (Rhizoctonia solani*), *Peronospora manshurica, Phakopsora pachyrhizi, Phoma foveata, Phoma medicaginis, Phomopsis longicolla, Phytophthora cinnamomi, Phytophthora erythroseptica, Phytophthora fragariae, Phytophthora infestans, Phytophthora medicaginis, Phytophthora megasperma, Phytophthora palmivora, Podosphaera leucotricha, Pseudopeziza medicaginis, Puccinia graminis* subsp. *Tritici* (UG99), *Puccinia sorghi, Pyricularia grisea, Pyricularia oryzae, Pythium ultimum, Rhizoctonia solani, Rhizoctonia zeae, Rosellinia* sp., *Sclerotinia sclerotiorum, Sclerotinina trifoliorum, Sclerotium rolfsii, Septoria glycines, Septoria lycopersici, Setomelanomma turcica, Sphaerotheca macularis, Spongospora subterranea, Stemphylium* sp, *Synchytrium endobioticum, Thecaphora* (*Angiosorus*), *Thielaviopsis, Tilletia indica, Trichoderma viride, Ustilago maydis, Verticillium albo-atrum, Verticillium dahliae, Verticillium dahliae, Xanthomonas axonopodis, Xanthomonas oryzae* pv. *oryzae*.

In a preferred embodiment of the present invention, the methods and materials of the invention are useful in suppressing the development the pathogens *Aspergillus fumigatus, Botrytis cinerea, Cerpospora betae, Colletotrichum* sp., *Curvularia* spp., *Fusarium* sp., *Ganoderma boninense, Geotrichum candidum, Gibberella* sp., *Monographella* sp., *Mycosphaerella fijiensis, Phytophthora palmivora, Phytophthora ramorum, Penicillium* sp., *Pythium ultimum, Rhizoctonia solani, Rhizopus* spp., *Schizophyllum* spp., *Sclerotinia sclerotiorum, Stagnospora* sp., *Verticillium dahliae*, or *Xanthomonas axonopodis*. In a particularly preferred embodiment, the inventive methods and materials may be used to suppress the development of several plant pathogens of commercial importance, including *Fusarium graminearum* NRRL-5883, *Monographella nivalis* ATCC MYA-3968, *Gibberella zeae* ATCC-16106, *Stagnospora nodurum* ATCC-26369, *Colletotrichum graminicola* ATCC-34167, and *Penicillium* sp. pathogens.

Seed Coating Formulation

In a particularly preferred embodiment, the microbial compositions of the present invention are formulated as a seed treatment. It is contemplated that the seeds can be substantially uniformly coated with one or more layers of the microbial compositions disclosed herein using conventional methods of mixing, spraying or a combination thereof through the use of treatment application equipment that is specifically designed and manufactured to accurately, safely, and efficiently apply seed treatment products to seeds. Such equipment uses various types of coating technology such as rotary coaters, drum coaters, fluidized bed techniques, spouted beds, rotary mists or a combination thereof. Liquid seed treatments such as those of the present invention can be applied via either a spinning "atomizer" disk or a spray nozzle which evenly distributes the seed treatment onto the seed as it moves though the spray pattern. Preferably, the seed is then mixed or tumbled for an additional period of time to achieve additional treatment distribution and drying. The seeds can be primed or unprimed before coating with the inventive compositions to increase the uniformity of germination and emergence. In an alternative embodiment, a dry powder formulation can be metered onto the moving seed and allowed to mix until completely distributed.

Another aspect of the invention provides seeds treated with the subject microbial compositions. One embodiment provides seeds having at least part of the surface area coated with a microbiological composition according to the present invention. In a specific embodiment, the microorganism-treated seeds have a microbial spore concentration or microbial cell concentration from about $10^6$ to about $10^9$ per seed. The seeds may also have more spores or microbial cells per seed, such as, for example $10^{10}$, $10^{11}$ or $10^{12}$ spores per seed. The microbial spores and/or cells can be coated freely onto the seeds or, preferably, they can be formulated in a liquid or solid composition before being coated onto the seeds. For example, a solid composition comprising the microorganisms can be prepared by mixing a solid carrier with a suspension of the spores until the solid carriers are impregnated with the spore or cell suspension. This mixture can then be dried to obtain the desired particles.

In some other embodiments, it is contemplated that the solid or liquid microbial compositions of the present invention further contain functional agents capable of protecting seeds from the harmful effects of selective herbicides such as activated carbon, nutrients (fertilizers), and other agents capable of improving the germination and quality of the products or a combination thereof.

Seed coating methods and compositions that are known in the art can be particularly useful when they are modified by the addition of one of the embodiments of the present invention. Such coating methods and apparatus for their application are disclosed in, for example, U.S. Pat. Nos. 5,918,413; 5,554,445; 5,389,399; 4,759,945; and 4,465,017. Seed coating compositions are disclosed, for example, in U.S. Pat. Appl. No. US20100154299, U.S. Pat. Nos. 5,939,356; 5,876,739, 5,849,320; 5,791,084, 5,661,103; 5,580,544, 5,328,942; 4,735,015; 4,634,587; 4,372,080, 4,339,456; and 4,245,432, among others.

A variety of additives can be added to the seed treatment formulations comprising the inventive compositions. Binders can be added and include those composed preferably of an adhesive polymer that can be natural or synthetic without phytotoxic effect on the seed to be coated. The binder may be selected from polyvinyl acetates; polyvinyl acetate copolymers; ethylene vinyl acetate (EVA) copolymers; polyvinyl alcohols; polyvinyl alcohol copolymers; celluloses, including ethylcelluloses, methylcelluloses, hydroxymethylcelluloses, hydroxypropylcelluloses and carboxymethylcellulose; polyvinylpyrolidones; polysaccharides, including starch, modified starch, dextrins, maltodextrins, alginate and chitosans; fats; oils; proteins, including gelatin and zeins; gum arabics; shellacs; vinylidene chloride and vinylidene chloride copolymers; calcium lignosulfonates; acrylic copolymers; polyvinylacrylates; polyethylene oxide; acrylamide polymers and copolymers; polyhydroxyethyl acrylate, methylacrylamide monomers; and polychloroprene.

Any of a variety of colorants may be employed, including organic chromophores classified as nitroso; nitro; azo, including monoazo, bisazo and polyazo; acridine, anthraquinone, azine, diphenylmethane, indamine, indophenol, methine, oxazine, phthalocyanine, thiazine, thiazole, triarylmethane, xanthene. Other additives that can be added include trace nutrients such as salts of iron, manganese, boron, copper, cobalt, molybdenum and zinc. A polymer or other dust control agent can be applied to retain the treatment on the seed surface.

In some specific embodiments, in addition to the microbial cells or spores, the coating can further comprise a layer of adherent. The adherent should be non-toxic, biodegradable, and adhesive. Examples of such materials include, but are not limited to, polyvinyl acetates; polyvinyl acetate copolymers; polyvinyl alcohols; polyvinyl alcohol copolymers; celluloses, such as methyl celluloses, hydroxymethyl celluloses, and hydroxymethyl propyl celluloses; dextrins; alginates; sugars; molasses; polyvinyl pyrrolidones; polysaccharides; proteins; fats; oils; gum arabics; gelatins; syrups; and starches. More examples can be found in, for example, U.S. Pat. No. 7,213,367 and U.S. Pat. Appln. No. US20100189693.

Various additives, such as adherents, dispersants, surfactants, and nutrient and buffer ingredients, can also be included in the seed treatment formulation. Other conventional seed treatment additives include, but are not limited to, coating agents, wetting agents, buffering agents, and polysaccharides. At least one agriculturally acceptable carrier can be added to the seed treatment formulation such as water, solids or dry powders. The dry powders can be derived from a variety of materials such as calcium carbonate, gypsum, vermiculite, talc, humus, activated charcoal, and various phosphorous compounds.

In some embodiment, the seed coating composition can comprise at least one filler which is an organic or inorganic, natural or synthetic component with which the active components are combined to facilitate its application onto the seed. Preferably, the filler is an inert solid such as clays, natural or synthetic silicates, silica, resins, waxes, solid fertilizers (for example ammonium salts), natural soil minerals, such as kaolins, clays, talc, lime, quartz, attapulgite, montmorillonite, bentonite or diatomaceous earths, or synthetic minerals, such as silica, alumina or silicates, in particular aluminium or magnesium silicates.

The seed treatment formulation may further include one or more of the following ingredients: other pesticides, including compounds that act only below the ground; fungicides, such as captan, thiram, metalaxyl, fludioxonil, oxadixyl, and isomers of each of those materials, and the like; herbicides, including compounds selected from glyphosate, carbamates, thiocarbamates, acetamides, triazines, dinitroanilines, glycerol ethers, pyridazinones, uracils, phenoxys, ureas, and benzoic acids; herbicidal safeners such as benzoxazine, benzhydryl derivatives, N,N-diallyl dichloroacetamide, various dihaloacyl, oxazolidinyl and thiazolidinyl compounds, ethanone, naphthalic anhydride compounds, and oxime derivatives; chemical fertilizers; biological fertilizers; and biocontrol agents such as other naturally-occurring or recombinant bacteria and fungi from the genera *Rhizobium, Bacillus, Pseudomonas, Serratia, Trichoderma, Glomus, Gliocladium* and mycorrhizal fungi. These ingredients may be added as a separate layer on the seed or alternatively may be added as part of the seed coating composition of the invention.

Preferably, the amount of the novel composition or other ingredients used in the seed treatment should not inhibit germination of the seed, or cause phytotoxic damage to the seed.

The formulation that is used to treat the seed in the present invention can be in the form of a suspension; emulsion; slurry of particles in an aqueous medium (e.g., water); wettable powder; wettable granules (dry flowable); and dry granules. If formulated as a suspension or slurry, the concentration of the active ingredient in the formulation is preferably about 0.5% to about 99% by weight (w/w), preferably 5-40% or as otherwise formulated by those skilled in the art.

As mentioned above, other conventional inactive or inert ingredients can be incorporated into the formulation. Such inert ingredients include but are not limited to: conventional sticking agents; dispersing agents such as methylcellulose, for example, serve as combined dispersant/sticking agents for use in seed treatments; polyvinyl alcohol; lecithin, polymeric dispersants (e.g., polyvinylpyrrolidone/vinyl acetate); thickeners (e.g., clay thickeners to improve viscosity and reduce settling of particle suspensions); emulsion stabilizers; surfactants; antifreeze compounds (e.g., urea), dyes, colorants, and the like. Further inert ingredients useful in the present invention can be found in McCutcheon's, vol. 1, "Emulsifiers and Detergents," MC Publishing Company, Glen Rock, N.J., U.S.A., 1996. Additional inert ingredients useful in the present invention can be found in McCutcheon's, vol. 2, "Functional Materials," MC Publishing Company, Glen Rock, N.J., U.S.A., 1996.

The coating formulations of the present invention can be applied to seeds by a variety of methods, including, but not limited to, mixing in a container (e.g., a bottle or bag), mechanical application, tumbling, spraying, and immersion. A variety of active or inert material can be used for contacting seeds with microbial compositions according to the present invention, such as conventional film-coating materials including but not limited to water-based film coating materials such as SEPIRET™ (Seppic, Inc., N.J.) and OPA-COAT™ (Berwind Pharm. Services, P.A.)

The amount of a composition according to the present invention that is used for the treatment of the seed will vary depending upon the type of seed and the type of active ingredients, but the treatment will comprise contacting the seeds with an agriculturally effective amount of the inventive composition. As discussed above, an effective amount means that amount of the inventive composition that is sufficient to affect beneficial or desired results. An effective amount can be administered in one or more administrations.

In addition to the coating layer, the seed may be treated with one or more of the following ingredients: other pesticides including fungicides and herbicides; herbicidal safeners; fertilizers and/or biocontrol agents. These ingredients may be added as a separate layer or alternatively may be added in the coating layer.

The seed coating formulations of the present invention may be applied to the seeds using a variety of techniques and machines, such as fluidized bed techniques, the roller mill method, rotostatic seed treaters, and drum coaters. Other methods, such as spouted beds may also be useful. The seeds may be pre-sized before coating. After coating, the seeds are typically dried and then transferred to a sizing machine for sizing. Such procedures are known in the art.

The microorganism-treated seeds may also be enveloped with a film overcoating to protect the coating. Such overcoatings are known in the art and may be applied using fluidized bed and drum film coating techniques.

In another embodiment of the present invention, compositions according to the present invention can be introduced onto a seed by use of solid matrix priming. For example, a quantity of an inventive composition can be mixed with a solid matrix material and then the seed can be placed into contact with the solid matrix material for a period to allow the composition to be introduced to the seed. The seed can then optionally be separated from the solid matrix material and stored or used, or the mixture of solid matrix material plus seed can be stored or planted directly. Solid matrix materials which are useful in the present invention include polyacrylamide, starch, clay, silica, alumina, soil, sand, polyurea, polyacrylate, or any other material capable of absorbing or adsorbing the inventive composition for a time and releasing that composition into or onto the seed. It is useful to make sure that the inventive composition and the solid matrix material are compatible with each other. For example, the solid matrix material should be chosen so that it can release the composition at a reasonable rate, for example over a period of minutes, hours, or days.

In principle, any plant seed capable of germinating to form a plant can be treated in accordance with the invention. Suitable seeds include those of cereals, coffee, cole crops, fiber crops, flowers, fruits, legume, oil crops, trees, tuber crops, vegetables, as well as other plants of the monocotyledonous, and dicotyledonous species. Preferably, crop seeds are coated include, but are not limited to, bean, carrot, corn, cotton, grasses, lettuce, peanut, pepper, potato, rapeseed, rice, rye, *sorghum*, soybean, sugarbeet, sunflower, tobacco, and tomato seeds. Most preferably, barley or wheat (spring wheat or winter wheat) seeds are coated with the present compositions.

Preparing the Microbial Compositions According to the Present Invention

Cultures of the microorganisms may be prepared for use in the microbial compositions of the invention using standard static drying and liquid fermentation techniques known in the art. Growth is commonly effected in a bioreactor.

A bioreactor refers to any device or system that supports a biologically active environment. As described herein a bioreactor is a vessel in which microorganisms including the microorganism of the invention can be grown. A bioreactor may be any appropriate shape or size for growing the microorganisms. A bioreactor may range in size and scale from 10 mL to liter's to cubic meters and may be made of stainless steel or any other appropriate material as known and used in the art. The bioreactor may be a batch type bioreactor, a fed batch type or a continuous-type bioreactor (e.g., a continuous stirred reactor). For example, a bioreactor may be a chemostat as known and used in the art of microbiology for growing and harvesting microorganisms. A bioreactor may be obtained from any commercial supplier (See also Bioreactor System Design, Asenjo & Merchuk, CRC Press, 1995).

For small scale operations, a batch bioreactor may be used, for example, to test and develop new processes, and for processes that cannot be converted to continuous operations.

Microorganisms grown in a bioreactor may be suspended or immobilized. Growth in the bioreactor is generally under aerobic conditions at suitable temperatures and pH for growth. For the organisms of the invention, cell growth can be achieved at temperatures between 5 and 37° C., with the preferred temperature being in the range of 15 to 30° C., 15 to 28° C., 20 to 30° C., or 15 to 25° C. The pH of the nutrient medium can vary between 4.0 and 9.0, but the preferred operating range is usually slightly acidic to neutral at pH 4.0 to 7.0, or 4.5 to 6.5, or pH 5.0 to 6.0. Typically, maximal cell yield is obtained in 20-72 hours after inoculation.

Optimal conditions for the cultivation of the microorganisms of this invention will, of course, depend upon the particular strain. However, by virtue of the conditions applied in the selection process and general requirements of most microorganisms, a person of ordinary skill in the art would be able to determine essential nutrients and conditions. The microorganisms would typically be grown in aerobic liquid cultures on media which contain sources of carbon, nitrogen, and inorganic salts that can be assimilated by the microorganism and supportive of efficient cell growth. Preferred carbon sources are hexoses such as glucose, but other sources that are readily assimilated such as amino acids, may be substituted. Many inorganic and proteinaceous materials may be used as nitrogen sources in the growth process. Preferred nitrogen sources are amino acids and urea but others include gaseous ammonia, inorganic salts of nitrate and ammonium, vitamins, purines, pyrimidines, yeast extract, beef extract, proteose peptone, soybean meal, hydrolysates of casein, distiller's solubles, and the like. Among the inorganic minerals that can be incorporated into the nutrient medium are the customary salts capable of yielding calcium, zinc, iron, manganese, magnesium, copper, cobalt, potassium, sodium, molybdate, phosphate, sulfate, chloride, borate, and like ions. Without being limited thereto, use of potato dextrose liquid medium for fungal strains and R2A broth premix for bacterial strains is preferred.

Novel Plant Varieties

Also provided, in another aspect of the present invention, is a novel plant created by artificially introducing a microbial endophyte of the invention into a plant that is free of endophytic microorganisms. In some embodiments of this aspect, the microbial endophyte introduced into the plant may be an endophytic microorganism having a plant growth-promoting activity, a biological control activity, or a combination of both activities. A variety of methods previously found effective for the introduction of a microbial endophyte into cereal grass species are known in the art. Examples of such methods include those described in U.S. Pat. Appl. No. 20030195117A1, U.S. Pat. Appl. No. 20010032343A1, and U.S. Pat. No. 7,084,331, among others. It will become apparent to those skilled in the art that many of the aforementioned methods can be useful for the making of a novel plant of the invention.

After artificial infection, it is preferred that a DNA sequence of the isolated endophytic microorganism is amplified by PCR and the endophyte is confirmed by carrying out a homology search for the DNA sequence amplified. Further, it is preferred that a foreign gene that expresses an identifiable means is introduced into the above-mentioned endophytic microorganism, and the presence of the colonization of the above-mentioned endophytic microorganism infecting the plant is confirmed by the above-identifiable means using the foreign gene.

Plants Suitable for the Methods of the Invention

In principle, the methods and compositions according to the present invention can be deployed for any plant species. Monocotyledonous as well as dicotyledonous plant species are particularly suitable. The methods and compositions are preferably used with plants that are important or interesting for agriculture, horticulture, for the production of biomass used in producing liquid fuel molecules and other chemicals, and/or forestry.

Thus, the invention has use over a broad range of plants, preferably higher plants pertaining to the classes of *Angiospermae* and *Gymnospermae*. Plants of the subclasses of the *Dicotylodenae* and the *Monocotyledonae* are particularly suitable. Dicotyledonous plants belong to the orders of the *Aristochiales, Asterales, Batales, Campanulales, Cappa-* rales, Caryophyllales, Casuarinales, Celastrales, Cornales, Diapensales, Dilleniales, Dipsacales, Ebenales, Ericales, Eucomiales, Euphorbiales, Fabales, Fagales, Gentianales, Geraniales, Haloragales, Hamamelidales, Illiciales, Juglandales, Lamiales, Laurales, Lecythidales, Leitneriales, Magniolales, Malvales, Myricales, Myrtales, Nymphaeales, Papeverales, Piperales, Plantaginales, Plumbaginales, Podostemales, Polemoniales, Polygalales, Polygonales, Primulales, Proteales, Rafflesiales, Ranunculales, Rhamnales, Rosales, Rubiales, Salicales, Santales, Sapindales, Sarraceniaceae, Scrophulariales, Theales, Trochodendrales, Umbellales, Urticales, and Violales. Monocotyledonous plants belong to the orders of the *Alismatales, Arales, Arecales, Bromeliales, Commelinales, Cyclanthales, Cyperales, Eriocaulales, Hydrocharitales, Juncales, Lilliales, Najadales, Orchidales, Pandanales, Poales, Restionales, Triuridales, Typhales, and Zingiberales*. Plants belonging to the class of the *Gymnospermae* are *Cycadales, Ginkgoales, Gnetales*, and *Pinales*.

Suitable species may include members of the genus *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis,* and *Zea.*

The methods and compositions of the present invention are preferably used in plants that are important or interesting for agriculture, horticulture, biomass for the production of biofuel molecules and other chemicals, and/or forestry. Non-limiting examples include, for instance, *Panicum virgatum* (switchgrass), *Sorghum bicolor* (*sorghum*, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), *Pennisetum glaucum* (pearl millet), *Panicum* spp., *Sorghum* spp., *Miscanthus* spp., *Saccharum* spp., *Erianthus* spp., *Populus* spp., *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cordgrass), *Arundo donax* (giant reed), *Secale cereale* (rye), *Salix* spp. (willow), *Eucalyptus* spp. (eucalyptus), *Triticosecale* spp. (triticum—wheat X rye), Bamboo, *Carthamus tinctorius* (safflower), *Jatropha curcas* (Jatropha), *Ricinus communis* (castor), *Elaeis guineensis* (oil palm), *Phoenix dactylifera* (date palm), *Archontophoenix cunninghamiana* (king palm), *Syagrus romanzoffiana* (queen palm), *Linum usitatissimum* (flax), *Brassica juncea, Manihot esculenta* (cassava), *Lycopersicon esculentum* (tomato), *Lactuca saliva* (lettuce), *Musa paradisiaca* (banana), *Solanum tuberosum* (potato), *Brassica oleracea* (broccoli, cauliflower, brusselsprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), *Solanum melongena* (eggplant), *Papaver somniferum* (opium poppy), *Papaver orientale, Taxus baccata, Taxus brevifolia, Artemisia annua, Cannabis saliva, Camptotheca acuminate, Catharanthus roseus, Vinca rosea, Cinchona officinalis, Coichicum autumnale, Veratrum californica, Digitalis lanata, Digitalis purpurea, Dioscorea* spp., *Andrographis paniculata, Atropa belladonna, Datura stomonium, Berberis* spp., *Cephalotaxus* spp., *Ephedra sinica, Ephedra* spp., *Erythroxylum coca, Galanthus wornorii, Scopolia* spp., *Lycopodium serratum* (*Huperzia serrata*), *Lycopodium* spp., *Rauwolfia serpentina, Rauwolfia* spp., *Sanguinaria canadensis, Hyoscyamus* spp., *Calendula officinalis, Chrysanthemum parthenium, Coleus forskohlii, Tanacetum parthenium, Parthenium argentatum* (guayule), *Hevea* spp. (rubber), *Mentha spicata* (mint), *Mentha piperita* (mint), *Bixa orellana, Alstroemeria* spp., *Rosa* spp. (rose), *Dianthus caryophyllus* (carnation), *Petunia* spp. (*petunia*), *Poinsettia pulcherrima* (poinsettia), *Nicotiana tabacum* (tobacco), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple), *Hordeum vulgare* (barley), *Poa pratensis* (bluegrass), *Lolium* spp. (ryegrass), *Phleum pratense* (timothy), and conifers. Of interest are plants grown for energy production, so called energy crops, such as cellulose-based energy crops like *Panicum virgatum* (switchgrass), *Sorghum bicolor* (*sorghum*, sudangrass), *Miscanthus giganteus* (miscanthus), *Saccharum* sp. (energycane), *Populus balsamifera* (poplar), *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cord-grass), *Medicago sativa* (alfalfa), *Arundo donax* (giant reed), *Secale cereale* (rye), *Salix* spp. (willow), *Eucalyptus* spp. (eucalyptus), *Triticosecale* spp. (triticum-wheat X rye), and Bamboo; and starch-based energy crops like *Zea mays* (corn) and *Manihot esculenta* (cassava); and sugar-based energy crops like *Saccharum* sp. (sugarcane), *Beta vulgaris* (sugarbeet), and *Sorghum bicolor* (L.) *Moench* (sweet *sorghum*); and biofuel-producing energy crops like *Glycine max* (soybean), *Brassica napus* (canola), *Helianthus annuus* (sunflower), *Carthamus tinctorius* (safflower), *Jatropha curcas* (Jatropha), *Ricinus communis* (castor), *Elaeis guineensis* (African oil palm), *Elaeis oleifera* (American oil palm), *Cocos nucifera* (coconut), *Camelina sativa* (wild flax), *Pongamia pinnata* (Pongam), *Olea europaea* (olive), *Linum usitatissimum* (flax), *Crambe abyssinica* (Abyssinian-kale), and *Brassica juncea*.

The discussion of the general methods given herein is intended for illustrative purposes only. Other alternative methods and embodiments will be apparent to those of skill in the art upon review of this disclosure, and are to be included within the spirit and purview of this application.

It should also be understood that the following examples are offered to illustrate, but not limit, the invention.

EXAMPLES

Example 1: Microorganism Isolation from Environmental Samples

Identification of Spore-Forming Rhizobacteria Using a Sonicated Roots and Serial Dilutions Method.

The following microorganisms were isolated using a "sonicated roots, serial dilutions" method as described below: the SGI-026-G06 and SGI-026-G07 isolates, which were isolated from a needle-like grass sample; the SGI-041-B03 isolate, which was isolated from a wild rye sample; and the SGI-020-A01 isolate, which was isolated from a wheat root tissues grown in a composite soil sample.

An enrichment procedure was developed to specifically identify spore-forming rhizobacteria. Briefly, sonicated root extracts were heat treated to kill vegetative cells and then plated onto a rich medium. Microorganisms that survived the heat treatment and formed colonies were considered to be spore-formers. This method was found to be particularly effective for selection of Gram-positive bacteria. Freshly sampled roots were used as starting material for these enrichments. Fine sections found at the tip of roots are the youngest, can have a high root hair density, and typically have high densities of rhizobacteria. A sterile blade was used to section these areas of the roots into 5-10 cm segments, which were then washed under sterile milliQ water to remove large soil particles. When needed, a more rigorous wash was accomplished by placing the roots into a 50 mL Falcon tube with 25 mL 1× sterile phosphate buffered saline (i.e. PBS buffer) and vortexing for 1 minute. Each root sample was subsequently suspended in 20 mL sterile PBS buffer and sonicated on ice for two 1-minute intervals at 8 watts using a Fisher Scientific Sonic Dismembrator. For heat treatment, typically 1 mL of the sonicated root cell suspension was transferred into a sterile Eppendorf tube incubated in an 80° C. water bath for 20 minutes. The heat treated cell suspensions were allowed to cool to room temperature before serially diluted to concentrations of $10^{-1}$, $10^{-2}$, $10^{-3}$, $10^{-4}$, $10^{-5}$, $10^{-6}$, and $10^{-7}$. 100 µL of each 10-fold dilution was spread onto culture plates containing a microbiological medium solidified with agar and 100 mg/L cycloheximide to inhibit fungal growth. In some cases, it was necessary to perform a 1/10 or 1/100 dilution prior to plating in order to obtain the proper CFU density for colony picking Isolated colonies were picked using sterile pipette tips, arrayed into 96-well microtiter plates each containing 150 µL 2×YT liquid medium per well. The microtiter plates were incubated for 1-2 days at 30° C. in order to obtain a high cell density for further characterization and archiving.

Isolation of Biofilm-Forming Bacteria.

The following microbial isolates were isolated using a "biofilm former" method as described below: the SGI-003-H11 isolate, which was isolated from a *Yucca* plant root sample; the SGI-034-009 isolate, which was isolated from a grass root sample; and the SGI-034-E10 isolate, which was from a Queen Anne's Lace plant sample.

Biofilm former method: In this procedure, biofilm-forming bacteria were isolated from sonicated root segments, as described by Fall et al. (*Syst. Appl. Microbiol.* 27, 372-379, 2004). As described above, bacteria that form biofilms the surface of a root are typically very good root colonizing bacteria, In general, when such bacteria are present at high densities, they can have a significant influence on plant health and can competitively exclude invading pathogens. Briefly, sonication was used to remove bacterial and fungal cells that are loosely attached to the root, leaving behind only those microbes that were strongly adhered to the root surface. Both Gram-positive and Gram-negative biofilm-forming bacteria were selected using this method.

Freshly sampled roots were used as starting material for these enrichments. Fine sections found at the tip of roots were the youngest tissues, had a high root hair density and typically had high densities of rhizobacteria. A sterile blade was used to section these areas of the roots into 5-10 cm segments, which were then washed by placing them into a 50 mL Falcon tube with 25 mL 1×PBS and vortexed for 1 minute. The debris from the wash was allowed to settle, and then a sterile forceps was used to transfer the washed root segments to 50 mL Falcon tubes filled with 25 mL 1×PBS, and sonicated on ice using a Fisher Scientific Sonic Dismembrator for two 30 second intervals with a 30 second pause between bursts. The sonicated root samples were transferred to sterile plastic Petri dishes and allowed to dry completely without lids inside a biosafety cabinet. Each root segment was then placed onto a separate CMA plate containing 1% agar (10 g/L Casein digest, 10 g/L mannitol, 10 g/L agar). Sometimes, a sterile forceps was used to push the root segment into the agar media. The plates were subsequently incubated at 37° C. and monitored for microbial growth. Typically after 1-2 days, multiple microbial growths emerged from the root and onto the CMA media. A sterile pipette tip was used to pick growths with unique morphologies along the segment and each of these growths was transferred to the center of a CMA plate containing 0.3% agarose. The CMA plates were subsequently incubated for 1-2 days at 37° C. and monitored for growth. Typically, biofilm-forming isolates displayed dendritic growth on this medium.

A sterile loop was used to transfer biomass and streak-purify each isolate from the CMA plates onto CMKA plates (2% agar, 1.2 g/L K2HPO4). The CMKA medium restricts biofilm growth and allows for the picking of individual colonies for archiving.

Example 2: Growth and Storage of the Microbial Isolates

The isolated bacteria were stored as a pure culture. A bacterial colony was transferred to a vial containing R2A broth liquid medium (Tecknova) and allowed to grow at 30° C. with shaking at 250 rpm for two days. The culture was then transferred into vials containing 15% glycerol and stored at −80° C.

Example 3: DNA Extraction, Sequencing and Taxonomy

A 20 µl aliquot of bacterial cell suspension was transferred to a 96-well PCR plate containing 20 µl of a 2× lysis buffer (100 mM Tris HCL, pH 8.0, 2 mM EDTA, pH 8.0, 1% SDS, 400 µg/mL Proteinase K). Lysis conditions were as follows: 55° C. incubation for 30 minutes, followed by 94° C. incubation for 4 minutes. An aliquot of the lysis product was used as the source of template DNA for PCR amplification.

For amplification of 16S rRNA region, each PCR mixture was prepared in a 20 µl final volume reaction containing 4 µl of the bacterial lysis reaction, 2 µM of each PCR primer, 6% Tween-20, and 10 µl of 2× ImmoMix (Bioline USA Inc, Taunton, Mass.). The primers used for PCR amplification were M13-27F (5'-TGTAAAACGACGGCCAGTTA-GAGTTTGATCCTGGCTCAG-3' SEQ ID NO: 8) and 1492R M13-tailed (5'-CAGGAAACAGCTATGACCGGT-TACCTTGTTACGACTT-3'; SEQ ID NO: 9). The PCR was carried out in a PTC-200 personal thermocycler (MJ-Research, MA, USA) as follows: 94° C. for 10 minutes; 94° C. for 30 seconds, 52° C. for 30 seconds, 72° C. for 75 seconds for 30 cycles; 72° C. for 10 minutes. A 2 µl aliquot of each PCR product was run on a 1.0% agarose gel to confirm a single band of the expected size. Positive bands were isolated, purified, and submitted for PCR sequencing. Sequencing was performed in the forward and reverse priming directions by the J. Craig Venter Institute in San Diego, Calif. using 454 technologies.

Homology search for the determined nucleotide sequence was conducted using the DDBJ/GenBank/EMBL database. Subsequently, the phylogenetic relationship of the nucleotide sequence of the 16 rRNA genes was analyzed among the isolated bacterial strains described herein, bacteria of the genera and species that exhibit high sequence homologies to the isolated bacterial strains, and other wide varieties of bacterial genera and species, using the ClustalW phylogenetic tree building program. Sequence identity and similarity were also determined using GenomeQuest™ software (Gene-IT, Worcester Mass. USA). The sequence analysis result revealed that the bacterial isolates SGI-003_H11, SGI-020_A01, SGI-026_G06, SGI-026_G07, SGI-034_C09, SGI-034_E10, SGI-041_B03 can be considered to be related to the species of *Pantoea agglomerans, Bacillus thuringiensis, Burkholderia metallica, Burkholderia vietnamiensis, Bacillus pumilus, Herbaspirillum* sp., *Pedobacter* sp., respectively, based upon >98% sequence homologies of each of the 16 rRNA sequences to the respective microorganisms.

Example 4: Biochemical Characteristics of the Bacterial Isolates

The isolated bacteria were further studied for properties important in their interaction with plants. The studied properties included nitrogen fixation, siderophore secretion, solubilization of inorganic phosphorus, production of 1-aminocyclopropane-1-carboxylic acid (ACC) deaminase, production of 2,3 butanediol, and the production of plant growth hormone auxin. The results of in vitro biochemical assays are shown in Table 2.

Nitrogen Fixation:

Bacterial cell suspensions were streaked on a solid medium of the following composition which did not include a nitrogen source: KOH 4.0 g/L; $K_2HPO_4$ 0.5 g/L; $MgSO_4.7H_2O$ 0.2 g/L; NaCl 0.1 g/L; $CaCl_2$ 0.02 g/L; $FeSO_4.7H_2O$ 0.005 g/L; $NaMo04.2H_2O$ 0.002 g/L; $MnSO4.7H_2O$ 0.01 g/L; Malic Acid 5.0 g/L; Gellan Gum 0.1-1.0 g/L; and optionally 0.5% v/v Bromothymol blue, pH 7.0. Gellan gum or agar concentrations may be varied as necessary to achieve desired medium thickness; typically 0.5 g/L was used. Streaks were incubated at 30° C. for 2-5 days. These plates were monitored daily and colonies were selected as they appeared. In some cases, longer growth periods (up to two weeks or greater) allowed for the capture of slower growing isolates. These streak plates were typically colony-picked using 20 or 200 μL aerosol barrier pipette tips into 96-well cell culture plates filled with 150 μL/well of 2YT medium. Alternatively, isolates were colony-picked from plates directly into N-free medium to confirm their N-free growth abilities. The results, as summarized in Table 2, indicated that only the isolate SGI-026_G07 showed nitrogen fixing activity at a detectable level.

Siderophore Secretion:

This assay was used to identify bacterial isolates that were producing siderophores, which are high-affinity $Fe^{3+}$-chelating compounds, in vitro. Typically, the microbial isolates were cultured on a minimal medium which was essentially free of Fe. All glassware used throughout this assay was acid-washed and rinsed three times with milliQ water to remove residual Fe which may alter assay results. The composition of the MM9 medium was as follows: $K_2HPO_4$ 0.5 g/L; $NH_4Cl$ 1.0 g/L; $MgSO_4.H_2O$ 0.2 g/L; NaCl 0.5 g/L; PIPES Buffer 7.55 g/L; Glucose 10.0 g/L; Gluconic Acid 2.5 g/L; Malic Acid 2.5 g/L; Casamino Acids 0.5 g/L. The medium was adjusted to pH 7.0 with 5N KOH, and sterilized using a 0.2 μM filter (Corning).

This assay was typically run in a high-throughput format using a Beckman FX liquid handling station and 96-well cell culture plates with 150 μL MM9 growth medium per well. Cultures and media were distributed and transferred aseptically using an autoclavable pin-tool under a laminar flow hood. Following transfer, cultures were incubated at 30° C. for 5 days. After incubation, the culture supernatants were harvested via centrifugation using a 96-well 0.22 μM filter plate. Ten microliters of filtered supernatant was transferred from each well to a Falcon assay plate. A standard curve was prepared using desferrioxamine (DFO) diluted in MM9 medium. Two-hundred microliters of the CAS assay solution [10 mM HDTMA, Fe(III)-Solution: 1 mM $FeCl_3.6H_2O$, 10 mM HCl, 2 mM CAS] was added to each of the supernatants and standard wells, followed by incubation at room temperature for 20-30 minutes. The absorbance of the blue CAS assay solution at 630 nm (SpectroMax M2) is inversely proportional to the siderophore concentration in each well (i.e., the assay solution should change to an intense orange with greater quantities of siderophores).

Solubilization of Inorganic Phosphorus:

The ability of the microbial isolates to solubilize mineral phosphate in vitro was assessed as follows. Bacteria to be tested were streaked on an agar phosphate growth medium [Hydroxylapatite—$Ca_{10}(PO_4)_5(OH)_2$ 5.0 g/L; $NH_4Cl$ 1.0 g/L; $MgSO_4.H_2O$ 0.2 g/L; NaCl 0.5 g/L; $FeSO_4.7H_2O$ 0.01 g/L; $Na_2MoO_4.7H_2O$ 0.01 g/L; $MnSO_4.7H_2O$ 0.01 g/L; Glucose 5.0 g/L; Gluconic Acid 2.5 g/L; Malic Acid 2.5 g/L; Casamino Acids 0.5 g/L; Gellan Gum 20.0 g/L; pH 7.2)], and their growth was monitored daily. The culture medium had an opaque appearance due the present of calcium phosphate. Bacterial growth and loss of the color of the medium would be observed if the bacteria have dissolving ability of calcium phosphate. Isolates having the ability to solubilize the mineral phase phosphate would produce a clear halo on the opaque medium surrounding the colony. As summarized in Table 2, the ability to solubilize mineral phosphate was not detectable in any of the tested microorganisms as determined by the in vitro assay described herein.

ACC Deaminase Production:

One of the major mechanisms utilized by plant growth-promoting rhizobacteria (PGPM) to facilitate plant growth and development is the lowering of ethylene levels by deamination of 1-aminocyclopropane-1-carboxylic acid (ACC), the immediate precursor of ethylene in plants. ACC deaminase catalyzes the hydrolysis of 1-aminocyclopropane-1-carboxylic acid (ACC) into α-ketobutyrate and ammonia. The presence of the α-ketobutyrate product can then be determined indirectly via a reaction with 2,4-dinitrophenylhydrazine in HCl to form a phenylhydrazone derivative. After an addition of NaOH, the amount of phenylhydrazone in solution can be determined spectrophotometrically by measuring its absorbance at 540 nm (Penrose and Glick, *Physiol Plant*. May; 118:10-1, 2003). This assay was typically run in a high-throughput format using 96-well cell culture plates. Each well contained 150 μL DF salts growth medium supplemented with 2.0 g/L $(NH_4)_2SO_4$. Cultures and media were distributed and transferred aseptically using an autoclavable pin-tool under a laminar-flow hood. Following transfer, cultures were incubated at 30° C. for 2 days. After reaching turbidity, the cultures were transferred a second time using a sterile pin-tool under a laminar-flow hood into 96-well plates containing 150 µL per well of DF salts growth medium supplemented with 5 mM ACC as the sole nitrogen source, followed by a 4 day incubation at 30° C. Absorbance of each culture at 600 nm was measured using a spectrophotometer. Isolates that displayed robust growth under these conditions (OD>0.2) were taken forward for further assay for ACC deaminase activity as described in Penrose and Glick, 2003, supra.

The test results, as summarized in Table 2, indicated that the following isolates produced significant amounts of ACC deaminase: SGI-003-H11, SGI-026-G06, SGI-026-G07, and SGI-041-B03.

2,3-Butanediol Production:

The ability of the bacterial isolates to synthesize 2,3-butanediol in vitro was assessed as follows using capillary gas chromatography mass spectroscopy as described by Ryu et al. (*Proc. Natl. Acad. Sci. U.S.A.* 100:4927-4932, 2003). This assay was typically run in a high-throughput format using 96-well cell culture plates with 150 µL DF salts growth medium per well. A titer-tek may also be used when preparing a large number of plates for primary screens of large isolate collections. Cultures and media were distributed and transferred aseptically using an autoclavable pin-tool under a laminar-flow hood. Following transfer, cultures were incubated at 30° C. for 5 days. After incubation, the culture supernatants were harvested via centrifugation using a 96-well 0.22 µM filter plate. Fifty microliters of filtered supernatant from each well was transferred to corresponding wells of a deep 96-well plate containing 450 µL 50% methanol per well using a L200 multichannel pipette and sealed with an adhesive plate seal, followed by 2,3-butanediol quantification assay using the protocol described by Ryu et al. (2003, supra). The test results, as summarized in Table 2, indicated that the following isolates produced significant amounts of 2,3-butanediol: SGI-003-H11, SGI-034-009, and SGI-041-B03.

Production of Auxin:

Auxins are hormones that can directly affect plant growth. This assay was performed to determine if the bacterial isolates produced auxins, since many rhizosphere and endophytic bacterial isolates are known to possess biochemical pathways that synthesize the auxin indole-3-acetic acid (IAA) and its derivatives. Tryptophan is often a precursor in this synthesis; and therefore, this assay quantified IAA (auxin) production from bacterial isolates grown on a medium supplemented with a low concentration of the amino acid tryptophan.

This assay was typically run in a high-throughput format using 96-well cell culture plates with 150 µL YT growth medium per well. When preparing a large number of plates for primary screens of large isolate collections, a titer-tek was used. Cultures and media were distributed and transferred aseptically using an autoclavable pin-tool under a laminar-flow hood. Following transfer, cultures were incubated at 30° C. for 5 days. After incubation, the culture supernatants were harvested via centrifugation using a 96-well 0.22 µM filter plate. Ten microliters of filtered supernatant from each well was transferred to a Falcon assay plate. Two hundred microliters of the Salkowsky's assay solution (Gordon and Weber, *Plant Physiol.* 26:192-195, 1951) was added to each of the supernatant and standard wells, followed by incubation at room temperature for 15-20 minutes. The reaction was monitored by absorbance of the plate on the SpectroMax M2 at 535 nm as color change from yellow to purple/pink of the Salkowsky's assay solution was proportional to the concentration of auxin (IAA) in each well. The test results, as summarized in Table 2, indicated that the following isolates produced significant amounts of the phytohormone auxin: SGI-003-H11, SGI-020-A01, SGI-034-009, SGI-034-009, and SGI-041-B03.

TABLE 2

Biochemical characteristics of the bacterial isolates (ND: not detectable).

| Bacterial Isolates | | Biochemical Activity | | | | |
| --- | --- | --- | --- | --- | --- | --- |
| Isolate ID | Provisional Taxonomy | Auxin production | ACC-deaminase | 2,3-butanediol | N-fixation | Phosphorus-solubilization |
| 003_H11 | *Pantoea agglomerans* | Yes | Yes | Yes | ND | ND |
| 020_A01 | *Bacillus thuringiensis* | Yes | ND | ND | ND | ND |
| 026_G06 | *Burkholderia metallica* | ND | Yes | ND | ND | ND |
| 026_G07 | *Burkholderia vietnamiensis* | ND | Yes | ND | Yes | ND |
| 034_C09 | *Bacillus pumilus* | Yes | ND | Yes | ND | ND |
| 034_E10 | *Herbaspirillum* sp. | ND | ND | ND | ND | ND |
| 041_B03 | *Pedobacter* sp. | Yes | Yes | Yes | ND | ND |

Example 5: Biocontrol Activity of the Bacterial Isolates Against Fungal Phytopathogens An in vitro antagonism assay was used to assess the ability of the isolated bacterial strains to suppress the development of several plant fungal pathogens, including *Fusarium graminearum* NRRL-5883, *Monographella nivalis* ATCC MYA-3968, *Gibberella zeae* ATCC-16106, *Stagnospora nodorum* ATCC-26369, *Colletotrichum graminicola* ATCC-34167, and a *Penicillium* sp. pathogen. The assay was performed on potato dextrose agar (PDA) medium. Isolated strains of bacteria were grown on one-fifth strength Tryptic soy broth agar (TSBA/5) for 24 h prior to use.

For each fungal pathogen, a conidial inoculum was produced by hyphal tipping an actively growing colony of the fungus and transferring the hyphal strands to PDA agar medium. After incubating the plates for 7 days at 25° C. using a 12 h/day photoperiod, fungal conidia were washed from PDA plates using a weak phosphate buffer (0.004% phosphate buffer, pH 7.2, with 0.019% $MgCl_2$). A suspension of fungal conidia in the weak phosphate buffer (approximately $1\times10^5$ conidia/mL) was then immediately sprayed over the agar surface, and the sprayed plates were then incubated at 25° C. for 48-72 h prior to use in antagonism tests.

To initiate the antagonism tests, cells of isolated microbial strains were point-inoculated at equal distances inside the perimeter of the plate. After five days, the bacterial strains were scored as antibiosis positive when a visibly clear area (i.e., growth inhibition zone) that lacked mycelial growth existed around the perimeter of the microbial colonies. The results of antagonism assays, as summarized in Table 3, demonstrated that each of the microorganisms disclosed herein inhibited the development of several fungal phytopathogens, including *Fusarium graminearum, Monographella nivalis, Gibberella zeae, Stagnospora nodurum, Colletotrichum graminicola, Penicillium* sp.

TABLE 3

Biocontrol activity of the bacterial isolates against fungal phytopathogens.

| Bacterial Isolates | | Growth suppression of fungal pathogen (inhibition zone scored after 5 days of incubation) | | | | | |
|---|---|---|---|---|---|---|---|
| Isolate ID | Provisional Taxonomy | *Fusarium graminearum* | *Monographella nivalis* | *Gibberella zeae* | *Stagnospora nodurum* | *Colletotrichum graminicola* | *Penicillium* sp. |
| 003_H11 | *Pantoea agglomerans* | No | Yes | No | No | No | No |
| 020_A01 | *Bacillus thuringiensis* | Yes | No | Yes | Yes | Yes | No |
| 026_G06 | *Burkholderia metallica* | No | Yes | Yes | Yes | Yes | Yes |
| 026_G07 | *Burkholderia vietnamiensis* | No | Yes | No | No | No | No |
| 034_C09 | *Bacillus pumilus* | No | No | No | Yes | No | No |
| 034_E10 | *Herbaspirillum* sp. | No | No | No | Yes | No | No |
| 041_B03 | *Pedobacter* sp. | No | Yes | No | Yes | Yes | Yes |

Example 6: Enhancement of Wheat Yield Potential

Effects of Bacterial Inoculation on Plant Growth and Yield were Studied in a greenhouse with the isolate SGI-020-A01. Microbial cell suspensions were prepared as follows. 2YT medium, or similar growth media, broth cultures were inoculated from the isolate's glycerol stocks or streak plates. Typically, prior to use in the growth chamber, greenhouse, or field, bacterial cultures were initiated 48-72 hours to allow the cultures to reach late exponential phase. Isolates that have longer doubling times were initiated further in advance. Cultures were incubated at 30° C. on a rotary shaker at 200 rpm. After growth, the cells were pelleted at 10,000×g for 15 min at 4° C. and resuspended in 10 mM $MgSO_4$ buffer (pH 7.0). Cell densities were normalized for each isolate on a CFU/mL basis. Typically, $\sim 10^9$ CFU/mL suspensions were prepared for each isolate and transported on ice to the inoculation site. Inoculations were performed by diluting these cell suspensions 1/20 in irrigation water to a final density $5 \times 10^7$ CFU/mL. For 1 liter pot trials, 20 mL of this dilute cell suspension was distributed evenly over the surface of each replicate pot.

Greenhouse trial was conducted with a nutrient deficient field soil. After removing large rocks and debris, field soil was mixed thoroughly to ensure homogeneity. After filling, soil in each of the pots was pressed down ~2 cm for a firm sowing layer. Seeds of a commercial wheat cultivar (hard red spring wheat; Howe Seeds, Inc.) were sown in 1 liter pots containing field soil medium (10.5 cm×12.5 cm tapered diameter plastic pots). Two grams of spring wheat seeds (approximately 70 seeds) were distributed evenly in each pot and 50 mL of field soil were applied and spread evenly over seed layer. Following uniform emergence of wheat coleoptile and subsequent emergence of first leaf, the plant population was inoculated with 20 mL of $10^9$ CFU/mL of SGI-020-A01. Plants of negative controls received 20 mL of inoculum buffer only. Each condition was performed in 8 replicate flats, each containing four 1 liter pots (n=4 per flat). The flats were randomly distributed over four experimental blocks. The seeds and plants were then maintained in a greenhouse for 60 days at ambient temperature (ranging from about 8° C. to about 22° C.) with diurnal light cycles of approximately 11.5 hours sunlight/12 hours dark throughout the trial. Plants were uniformly bottom watered to appropriate hydration level depending on the temperature and stage of growth. At approximately 30 days post sowing, approximately 70 individuals per pot were staked and loosely tied together to prevent cross contamination and to minimize positional effects due to variation in plants falling into other pots. At approximately 60 days post sowing, plants were allowed to dry out in preparation for harvest. Wheat heads were harvested at approximately 80 days post sowing. Each wheat head was removed by cutting just below the head. Wheat heads within each pot replicate were pooled, weighted, and subsequently used as an estimate of yield potential. All plants in the population were harvested on the same day and treatments were harvested in a randomized order to eliminate large differences in time in between harvesting between treatments. As a result, wheat plants treated with the isolate SGI-020-A01 showed a 40% increase in yield potential compared to control non-treated plants (2.95 gram/pot vs. 2.10 gram/pot). Averages and standard deviations were documented across all 8 replicates and an ANOVA (Analysis of Variance) was performed. Efficacy of the microbial isolate SGI-020-A01 in enhancing wheat yield potential was quantified by analyzing the wheat head yield in weight for each pot replicate. P-values of <0.05 were considered significant.

Example 7: Enhancement of Biomass Production in Maize

Effects of bacterial inoculation on plant growth and yield were studied in greenhouse experiments with each of the following bacterial isolates: SGI-034-009, SGI-034-E10, SGI-003-H11, SGI-041-B03, SGI-026-G06, and SGI-026-G07. The greenhouse trials were conducted with a nutrient deficient field soil. After removing large rocks and debris, field soil was mixed thoroughly with potting soil (70:30) to ensure homogeneity. After filling, soil in each of the pots was pressed down ~2 cm for a firm sowing layer. Seeds of a commercial maize cultivar (Dow AgroSciences) were sown in 1 liter pots (10.5 cm×12.5 cm tapered pots) each containing soil medium. Two maize kernels were distributed evenly in each pot in embryo-up orientation, followed by application of 50 mL of field soil, which was spread evenly over the seed layer. After germination, culling of one seedling per pot was performed if necessary so that each pot contained only one plant.

Following uniform emergence of maize coleoptile and subsequent emergence of first leaf, the plant population was inoculated with ~20 mL of $10^9$ CFU/ml of a microbial isolate selected from the group of SGI-034-009, SGI-034-E10, SGI-003-H11, SGI-041-B03, SGI-026-G06, and SGI-026-G07. Microbial cell suspensions were prepared as described in Example 6 above. Plants of negative controls received 20 mL of inoculum buffer only.

Each condition was performed in 8 replicate flats, each containing two 1 liter pots (n=2 per flat). The flats were randomly distributed over four experimental blocks. The seeds and plants were then maintained in a greenhouse for 60 days at ambient temperature (ranging from about 8° C. to about 22° C.) with diurnal light cycles of approximately 11.5 hours sunlight/12 hours dark throughout the trial. Plants were uniformly bottom watered to appropriate hydration level depending on the temperature and stage of growth. Maize above-ground biomass was harvested at approximately 60 days post sowing.

All plants in the population were harvested on the same day and treatments were harvested in a randomized order to eliminate large differences in time in between harvesting between treatments. Maize plants were analyzed for difference in total biomass. As documented in Table 4, maize plants treated with each of the microbial isolates showed a significant increase in total biomass as compared to control non-treated plants. Averages and standard deviations were documented across all 8 replicates and an ANOVA (Analysis of Variance) was performed.

TABLE 4

Efficacy of the microbial isolates in enhancing total plant biomass.

| Treatment | Plant biomass (g) | p-Value | Biomass Increase (%) |
| --- | --- | --- | --- |
| Non-treated | 58.6 | N/A | N/A |
| SGI-034-C09 | 106.3 | <.0001 | 181% |
| SGI-034-E10 | 103.6 | <.0001 | 177% |
| SGI-003-H11 | 100.7 | <.0001 | 172% |
| SGI-041-B03 | 99.5 | 0.0001 | 170% |
| SGI-026-G06 | 98.3 | 0.0002 | 168% |
| SGI-026-G07 | 97.3 | 0.0003 | 166% |

Example 8: Seed Coating Treatment of Wheat Seeds and Corn Seeds

Small scale seed treatment experiments were conducted by following a procedure described in Sudisha et al. (*Phytoparasitica,* 37:161-169, 2009) with minor modifications. Typically, a biopolymer stock solution was made by adding 1 gram of gum arabic powder (MP Biomedical) to 9 mL water and mixing to homogeneity. Turbid cultures of actively growing microbial cells or microbial spore preparations were washed with PBS and adjusted to an OD600 of ~5.0. Three mL of the adjusted cell suspension was pelleted via centrifugation in a 50 mL Falcon tube. The resulting supernatant was decanted, replaced with 3 mL biopolymer stock solution and the resulting suspension was mixed thoroughly. Typically, approximately 25 g of seeds were added to the Falcon tube and vigorously shaken or vortexed to ensure a uniform distribution of the gum/cell suspension. Coated seeds were spread across plastic weigh boats to dry in a laminar flow hood until no longer tacky, generally 3 hours with periodic mixing. The coated seeds were then stored at 4° C. and periodically tested for stability. A variety of wheat seeds and corn seeds were coated and tested in the manner described above, including common hard red spring wheat varieties Briggs, Faller, Glenn, Hank, RB07, Samson; hard red winter wheat varieties Jerry, McGill, Overland; and maize seed variety DKC62-61 as well as a commercial maize cultivar (Dow AgroSciences).

Viability testing on the microbes used in seed coating formulation was performed using a standard plate count method. Typically, a pre-determined amount of coated seeds was tested for the presence of viable microbes by washing the seeds in an aliquot of appropriate buffer and plating equivalent amounts of buffer on nutrient agar media. Viable colony-forming-units were determined after 1-4 days incubation at 30° C. Viability test showed that between $1\times10^4$ and $4\times10^7$ viable colony-forming-units per seed were present after approximately five weeks of storage at 4° C. When seeds were coated with microbial spores, the viability of the majority of tested microbes remained stable for at least four months, including multiple interstate shipments across the United States, in and out of refrigerated containers. When stored under refrigeration (4° C.) the microbes survived on the seed coat with little loss in viability over the test periods. The results indicated that seeds coated with compositions disclosed herein could be stored for extended periods under refrigeration and suggested that microbes would survive during periods of higher temperatures for distribution. In addition, germination rate of the coated seeds was tested and determined to be essentially identical to control seeds, which were either seeds coated with gum arabic only or uncoated seeds.

Example 9: Solid State Formulation of the Microbial Compositions

This section describes an exemplary formulation of a microbial fertilizer where the bacteria in accordance with the present invention are encapsulated and the fertilizer is in solid form. Alginate beads are prepared as follows:

One milliliter of 30% glycerol is added to 1, 1.5 or 2% sodium alginate solution, depending on the alginate properties (M/G ratio) to obtain a final volume of 25 mL. Bacterial cells from a 250 mL culture obtained from one of the bacterial isolates of the invention or from a combination of two or more isolates is pelleted via centrifuged, then washed with a saline solution (0.85% NaCl, w/v), suspended in 25 mL of alginate mixture, and mixed thoroughly. This cell suspension is then added drop wise into a pre-cooled sterile 1.5 or 2% (w/v) aqueous solution of $CaCl_2$ under mild agitation to obtain the bacterial-alginate beads. These beads are allowed to harden for 2-4 h at room temperature. Beads are collected by sieving and are washed several times with sterile water and stored at 4° C. In order to preserve the formulation, the fresh wet beads can be frozen at about −80° C. prior to lyophilization at about −45° C. for 15 h. The lyophilized dry beads can be stored in appropriate containers, such as sterile glass bottles.

To estimate the viable counts, the encapsulated bacteria can be released from the beads by resuspending 100 mg of beads in phosphate buffered saline (pH 7.0) for 30 min followed by homogenization. The total number of released bacteria is determined by standard plate count method after incubating at 30° C. for 48 h. At one month intervals the cell densities in the beads are enumerated using similar method.

Example 10: Compatibility of the Microbial Compositions with Commercial Fungicides As environmental concerns are increasing about using pesticides in agriculture, biological alternatives are increasingly perceived as inevitable. However, new biological formulations must also allow organisms to survive and express their specific beneficial impact. Chemical fungicides are generally toxic not only towards deleterious microorganisms but also to the beneficial ones. However, chance of survivability of these microbial agents might have been enhanced when applied at reduced rates.

In the present study, peat-based carrier material is used for inoculation of both the fungicide treated as well as bare crop seed. Bacterial tolerability of fungicide is generally evaluated in the following manner: a) bacteria inoculated bare seeds grown on an appropriate bacterial growth medium such as trypticase soy agar (TSA; Tryptone 15 g/L; Soytone 5 g/L, sodium chloride 5 g/L, and agar 15 g/L) plates, b) fungicide-treated bacteria inoculated seeds grown on common TSA plates, and, c) fungicide-treated bacteria inoculated seeds grown in the sterile growth pouches. Typically, three concentrations of fungicide are used in each of the experiments: manufacturer's recommended dose and two lower doses (at 75% and 50% of the recommended dose). Fungicide-treated bacteria inoculated seeds are stored after inoculation and used at different time intervals (2 hrs, 4 hrs and 6 hrs) to examine the impact on seed germination. Both seed germination and bacterial presence are monitored in petri-plates. For the growth pouch study, fungicide-treated (recommended dose) seeds are used, and root and hypocotyl lengths were measured at 7 days of seedling growth.

Some rhizobacterial isolates of the invention are compatible with several commonly used fungicides as determined by bacterial growth on fungicide-enriched TSA plates. In general, both bare and fungicide-treated seeds, coated with inoculated peat show no significant variation in germination compared to non-inoculated control. Moreover, growth-promoting effects on root and total seedling lengths are observed in all rhizobacterial treatments compared to non-inoculated control.

Example 11: Development of Non-Naturally Occurring Cultivars and Breeding Program Endophytic bacteria of the present invention are introduced into crop plants, including cereals, of varying genotypes and geographic origin, lacking such endophytic fungi, to create plant-endophyte combinations with improved agronomic characteristics, using procedures analogous to those known in the art, including those described in U.S. Pat. Appl. No. 20030195117A1; U.S. Pat. Appl. No. 20010032343A1; and U.S. Pat. No. 7,084,331, among others. Thus, synthetic plant-endophyte combinations may be created and selected in a breeding/cultivar development program based on their ability to form and maintain a mutualistic combination that results in an agronomic benefit. Rating of agronomic characteristics of the combination may also be utilized in such a breeding program. These characteristics may include, without limitation, drought tolerance, biomass accumulation, resistance to insect infestation, palatability to livestock (e.g., herbivores), ease of reproduction, and seed yield, among others. Such combinations may differ in levels of accumulation of microbial metabolites that are toxic to pests and weeds, including ergot alkaloid levels, loline levels, peramine levels, or lolitrem levels, while displaying desired agronomic characteristics of crop plants, including resistance to insect feeding or infestation, resistance to abiotic stress, palatability to livestock, biomass accumulation, ease of reproduction, and seed yield, among other traits.

Example 12: Yield Study

Corn seeds (*Zea mays*) were coated with different microbial treatments and sown in a prepared field. Each treatment was replicated 5 times in random complete block design. A single replicate consisted of four 30 feet long beds (rows), 60 seeds were sown (6 inches apart) in each bed. For the observation purpose data was taken from the middle two rows only.

Plant emergence was recorded twice as shown in Table 5 below as the percentage of plants in the replicate that had sprouted. Ten plants in the middle two rows of each plot were tagged with a plastic ribbon to record the vital statistics such as the plant height, chlorophyll measurement, plant weight etc. of the plants.

The plant heights (measuring the tip of the tallest/longest leaf) recorded 31 and 56 days after planting indicated that the plant height among the treatments was not significantly different. Most of the plants were dry and leaves had shrunk by day 110 post planting, therefore, in some of the cases, plants looked (measured) shorter than in previous measurement, but overall, the plant height did not differ among the treatments. On the 5th week of planting, chlorophyll content was measured (in SPAD units) from the lower leaves (ca. 60 cm above the ground) and upper leaves (second fully expanded leaf from the top) of ten tagged plants of each plot. The chlorophyll content among the treatments did not significantly differ. On the 110th and 111th day of planting, the crop was harvested. Ten tagged plants from each plot were cut at the soil level and above the ground parts of the plants were weighed (whole plant weight or WPtWt), corn ears were removed and the length of the cob was measured (ear length with kernels) (region filled with marketable kernels only), then the kernels were removed from the cob and their weight was measured for the kernel weight per ear (KnlWt/ear).

Shortly after the manual harvest of 10 plants per plot was over, a mechanical harvester, Gleaner® K2 (Allis-Chalmers Mfrg, Milwaukee, Wis.) was brought in. This machine mechanically removed the remaining plants from two middle rows of each plot, removed the kernels from the cobs, and took the measurement of kernel moisture and weight (10 ears+machine harvest). The projected total yield at 15.5% moisture content (pounds of corn kernel per acre) based on the weight (lb.) of kernels (include kernels from machine harvested cobs+manual harvested cobs) was 10368.14 pounds per acre or 185.15 bushels per acre for SGI-003-H11 (*Pantoea agglomerans*). This was the highest yield among all organism treatments and significantly different from the treatments for *Bacillus amyloliquefaciens* SGI-015_F03. The other high producer was the treatment with *Bacillus thuringiensis* SGI-020_A01.

In conclusion, all the plants in the different treatments emerged and grew similarly in the field conditions provided with the same amount of fertilizer, pre-emergent herbicide (with manual weed pulling later in the season), and weekly irrigation during the growing and warm season, and pest control of especially the corn earworm. With all conditions equal, treatment with SGI-003-H11 (*Pantoea agglomerans*) produced the highest yield over the non-microbe, control treatment. Thus, 003_H11 produced a yield of approximately 17% higher than the control group. Thus, in various embodiments of the invention application of an effective amount of the organism according to any of the methods described herein produces at least 10% or at least 12.5% or at least 15% or about 17% higher yield than a control group, which in some embodiments can be determined by pounds of plant product (e.g., corn ears) per acre or bushels of plant product per acre. Organisms listed in Table 5 are SGI-003-H11 (*Pantoea agglomerans*); SGI-015-F03 (*Bacillus amyloliquefaciens*); and SGI-020-A01 (*Bacillus thuringiensis*).

TABLE 5

| Organism | Emergence | Emergence | Height | Height | Height |
|---|---|---|---|---|---|
| Date | 6/20 | 6/24 | 7/11 | 8/5 | 9/28 |
| Control | 97.00 | 94.50 | 103.64 | 277.22 | 267.82 |
| SGI-003-H11 | 89.50 | 93.34 | 103.32 | 273.58 | 272.04 |
| SGI-015-F03 | 95.67 | 96.67 | 105.02 | 282.02 | 276.08 |
| SGI-020-A01 | 94.83 | 95.33 | 102.04 | 268.94 | 264.80 |

TABLE 5-continued

| Organism | Upper Leaf | Lower Leaf | WPtWt | Ear Length w/knls |
|---|---|---|---|---|
| Date | 7/18 | 7/18 | 9/28 | 9/28 |
| Control | 43.24 | 60.85 | 493.24 | 14.98 |
| SGI-003-H11 | 44.17 | 59.43 | 494.92 | 14.29 |
| SGI-015-F03 | 44.90 | 63.96 | 473.40 | 14.45 |
| SGI-020-A01 | 46.45 | 63.84 | 488.30 | 14.20 |

| Organism | Knl wt/ear(g) | Knl wt/ear(lb) | 10 ears + machine | 10 ears + machine |
|---|---|---|---|---|
| Date | 9/28 | 9/28 | 9/29 | 9/29 |
| Control | 168.62 | 0.37 | 157.81 | 8837.63 |
| SGI-003-H11 | 171.96 | 0.38 | 185.15 | 10368.14 |
| SGI-015-F03 | 156.24 | 0.34 | 161.17 | 9025.62 |
| SGI-020-A01 | 158.68 | 0.35 | 163.09 | 9133.16 |

A number of embodiments of the invention have been described. Nevertheless, it will be understood that elements of the embodiments described herein can be combined to make additional embodiments and various modifications may be made without departing from the spirit and scope of the invention. Accordingly, other embodiments, alternatives and equivalents are within the scope of the invention as described and claimed herein.

Headings within the application are solely for the convenience of the reader, and do not limit in any way the scope of the invention or its embodiments.

All publications and patent applications mentioned in this specification are herein incorporated by reference to the same extent as if each individual publication or patent application was specifically can individually indicated to be incorporated by reference.

What is claimed is:

1. A coated plant seed having a coating comprising a carrier and an endophyte, wherein the endophyte comprises microbial strain SGI-003-H11, deposited as NRRL B-50483.

2. The coated plant seed of claim 1, further comprising an agriculturally effective amount of a compound selected from the group consisting of a fertilizer, an acaricide, a bactericide, a fungicide, an insecticide, a microbicide, a nematicide and a pesticide.

3. The coated plant seed of claim 1, wherein said composition is a seed coating formulation.

4. The coated plant seed of claim 1, wherein said composition is prepared as a formulation selected from the group consisting of an emulsion, a colloid, a dust, a granule, a pellet, a powder, a spray and a solution.

5. The coated plant seed of claim 1, wherein said plant seed is a corn plant seed or a wheat plant seed.

6. The plant seed of claim 1, wherein the microbial strain SGI-003-H11 comprises a nucleotide sequence that exhibits at least 90% identity to SEQ ID NO:1.

7. The plant seed of claim 1, wherein the microbial strain SGI-003-H11 comprises a nucleotide sequence that exhibits at least 99% identity to SEQ ID NO:1.

8. The plant seed of claim 1, wherein the microbial strain SGI-003-H11 comprises the nucleotide sequence comprising SEQ ID NO:1.

9. A method for producing the coated plant seed of claim 1, said method comprising a step of exposing or contacting said plant seed with said microbial strain SGI-003-H11, deposited as NRRL B-50483, wherein the coated plant seed is produced.

10. A method for inhibiting or treating the development of a pathogenic disease of a plant caused by a plant pathogen, said method comprising growing a plant from the coated seed of claim 1.

11. The method according to claim 10, wherein said plant pathogen is selected from the group consisting of *Colletotrichum, Monographella, Penicillium*, and *Stagnospora* organisms.

12. The method according to claim 10, wherein said plant pathogen is selected from the group consisting of *Colletotrichum graminicola, Monographella nivalis, Penicillium* sp., or *Stagnospora noduruin.*

13. The method according to claim 10, wherein said microbial strain is additionally applied to soil or a plant or plant part thereof grown from said coated seed.

* * * * *

SEQUENCE LISTING

```
<160> NUMBER OF SEQ ID NOS: 11

<210> SEQ ID NO 1
<211> LENGTH: 1436
<212> TYPE: DNA
<213> ORGANISM: Pantoea agglomerans
<220> FEATURE:
<221> NAME/KEY: misc_feature
<223> OTHER INFORMATION: SGI bacterial isolate SGI-003_H11
<220> FEATURE:
<221> NAME/KEY: misc_feature
<223> OTHER INFORMATION: encodes a 16S ribosomal RNA
<220> FEATURE:
<221> NAME/KEY: misc_feature
<222> LOCATION: (62)..(63)
<223> OTHER INFORMATION: n is a, c, g, or t

<400> SEQUENCE: 1
gctggcggca ggcctaacac atgcaagtcg agcggtagca cagagagctt gctctcgggt      60
gnngagcggc ggacgggtga gtaatgtctg ggaaactgcc tgatggaggg ggataactac     120
tggaaacggt agctaatacc gcataacgtc gcaagaccaa agtgggggac cttcgggcct     180
catgccatca gatgtgccca gatgggatta gctagtaggt gaggtaatgg ctcacctagg     240
cgacgatccc tagctggtct gagaggatga ccagccacac tggaactgag acacggtcca     300
gactcctacg ggaggcagca gtggggaata ttgcacaatg ggcgcaagcc tgatgcagcc     360
atgccgcgtg tatgaagaag gccttcgggt tgtaaagtac tttcagcgag gaggaaggcg     420
ataaggttaa taaccttgtc gattgacgtt actcgcagaa gaagcaccgg ctaactccgt     480
gccagcagcc gcggtaatac ggagggtgca agcgttaatc ggaattactg ggcgtaaagc     540
```

-continued

```
gcacgcaggc ggtctgtcaa gtcggatgtg aaatccccgg gctcaacctg ggaactgcat    600
ccgaaactgg caggctagag tcttgtagag gggggtagaa ttccaggtgt agcggtgaaa    660
tgcgtagaga tctggaggaa taccggtggc gaaggcggcc ccctggacaa agactgacgc    720
tcaggtgcga aagcgtgggg agcaaacagg attagatacc ctggtagtcc acgctgtaaa    780
cgatgtcgac ttggaggttg ttcccttgag gagtggcttc cggagctaac gcgttaagtc    840
gaccgcctgg ggagtacggc cgcaaggtta aaactcaaat gaattgacgg gggcccgcac    900
aagcggtgga gcatgtggtt taattcgatg caacgcgaag aaccttacct actcttgaca    960
tccagagaac ttagcagaga tgctttggtg ccttcgggaa ctctgagaca ggtgctgcat   1020
ggctgtcgtc agctcgtgtt gtgaaatgtt gggttaagtc ccgcaacgag cgcaaccctt   1080
atcctttgtt gccagcggtt cggccgggaa ctcaaaggag actgccagtg ataaactgga   1140
ggaaggtggg gatgacgtca agtcatcatg gcccttacga gtagggctac acacgtgcta   1200
caatggcata tacaaagaga agcgacctcg cgagagcaag cggacctcat aaagtatgtc   1260
gtagtccgga tcggagtctg caactcgact ccgtgaagtc ggaatcgcta gtaatcgtgg   1320
atcagaatgc cacggtgaat acgttcccgg gccttgtaca caccgcccgt cacaccatgg   1380
gagtgggttg caaaagaagt aggtagctta accttcggga gggcgcttac cacttt       1436
```

```
<210> SEQ ID NO 2
<211> LENGTH: 1440
<212> TYPE: DNA
<213> ORGANISM: Bacillus thuringiensis
<220> FEATURE:
<221> NAME/KEY: misc_feature
<223> OTHER INFORMATION: SGI bacterial isolate SGI-020_A01
<220> FEATURE:
<221> NAME/KEY: misc_feature
<223> OTHER INFORMATION: encodes a 16S ribosomal RNA

<400> SEQUENCE: 2
```

```
cgtgcctaat acatgcaagt cgagcgaatg gattaagagc ttgctcttat gaagttagcg     60
gcggacgggt gagtaacacg tgggtaacct gcccataaga ctgggataac tccgggaaac    120
cggggctaat accggataat attttgaact gcatggttcg aaattgaaag gcggcttcgg    180
ctgtcactta tggatggacc cgcgtcgcat tagctagttg gtgaggtaac ggctcaccaa    240
ggcaacgatg cgtagccgac ctgagagggt gatcggccac actgggactg agacacggcc    300
cagactccta cgggaggcag cagtagggaa tcttccgcaa tggacgaaag tctgacggag    360
caacgccgcg tgagtgatga aggctttcgg gtcgtaaaac tctgttgtta gggaagaaca    420
agtgctagtt gaataagctg gcaccttgac ggtacctaac cagaaagcca cggctaacta    480
cgtgccagca gccgcggtaa tacgtaggtg gcaagcgtta tccggaatta ttgggcgtaa    540
agcgcgcgca ggtggtttct taagtctgat gtgaaagccc acggctcaac cgtggagggt    600
cattggaaac tgggagactt gagtgcagaa gaggaaagtg gaattccatg tgtagcggtg    660
aaatgcgtag agatatggag gaacaccagt ggcgaaggcg actttctggt ctgtaactga    720
cactgaggcg cgaaagcgtg gggagcaaac aggattagat accctggtag tccacgccgt    780
aaacgatgag tgctaagtgt tagagggttt ccgcccttta gtgctgaagt taacgcatta    840
agcactccgc ctggggagta cggccgcaag gctgaaactc aaaggaattg acgggggccc    900
gcacaagcgg tggagcatgt ggtttaattc gaagcaacgc gaagaacctt accaggtctt    960
gacatcctct gaaaacccta gagatagggc ttctccttcg ggagcagagt gacaggtggt   1020
gcatggttgt cgtcagctcg tgtcgtgaga tgttgggtta agtcccgcaa cgagcgcaac   1080
```

```
ccttgatctt agttgccatc attaagttgg gcactctaag gtgactgccg gtgacaaacc    1140
ggaggaaggt ggggatgacg tcaaatcatc atgcccctta tgacctgggc tacacacgtg    1200
ctacaatgga cggtacaaag agctgcaaga ccgcgaggtg gagctaatct cataaaaccg    1260
ttctcagttc ggattgtagg ctgcaactcg cctacatgaa gctggaatcg ctagtaatcg    1320
cggatcagca tgccgcggtg aatacgttcc cgggccttgt acacaccgcc cgtcacacca    1380
cgagagtttg taacacccga agtcgtggg gtaaccttt tggagccagc cgcctaaggt    1440
```

<210> SEQ ID NO 3
<211> LENGTH: 1414
<212> TYPE: DNA
<213> ORGANISM: Burkholderia metallica
<220> FEATURE:
<221> NAME/KEY: misc_feature
<223> OTHER INFORMATION: SGI bacterial isolate SGI-026_G06
<220> FEATURE:
<221> NAME/KEY: misc_feature
<223> OTHER INFORMATION: encodes a 16S ribosomal RNA

<400> SEQUENCE: 3

```
catgcaagtc gaacggcagc acgggtgctt gcacctggtg gcgagtggcg aacgggtgag      60
taatacatcg gaacatgtcc tgtagtgggg gatagcccgg cgaaagccgg attaataccg     120
catacgatct acggatgaaa gcggggggacc ttcgggcctc gcgctatagg gttggccgat     180
ggctgattag ctagttggtg gggtaaaggc ctaccaaggc gacgatcagt agctggtctg     240
agaggacgac cagccacact gggactgaga cacggcccag actcctacgg gaggcagcag     300
tggggaattt tggacaatgg gcgaaagcct gatccagcaa tgccgcgtgt gtgaagaagg     360
ccttcgggtt gtaaagcact tttgtccgga agaaatcct tgattctaat acagtcgggg     420
gatgacggta ccggaagaat aagcaccggc taactacgtg ccagcagccg cggtaatacg     480
tagggtgcga gcgttaatcg gaattactgg gcgtaaagcg tgcgcaggcg gtttgctaag     540
accgatgtga atccccgggg ctcaacctgg gaactgcatt ggtgactggc aggctagagt     600
atggcagagg ggggtagaat tccacgtgta gcagtgaaat gcgtagagat gtggaggaat     660
accgatggcg aaggcagccc cctgggccaa tactgacgct catgcacgaa agcgtgggga     720
gcaaacagga ttagatacc tggtagtcca cgccctaaac gatgtcaact agttgttggg     780
gattcatttc cttagtaacg tagctaacgc gtgaagttga ccgcctgggg agtacggtcg     840
caagattaaa actcaaagga attgacggg acccgcacaa gcggtggatg atgtggatta     900
attcgatgca acgcgaaaaa ccttacctac ccttgacatg tcggaatcc tgctgagagg     960 cgggagtgct cgaaagagaa ccggcgcaca ggtgctgcat ggctgtcgtc agctcgtgtc    1020
gtgagatgtt gggttaagtc ccgcaacgag cgcaacccctt gtccttagtt gctacgcaag    1080
agcactctaa ggagactgcc ggtgacaaac cggaggaagg tggggatgac gtcaagtcct    1140
catggccctt atgggtaggg cttcacacgt catacaatgg tcggaacaga gggttgccaa    1200
cccgcgaggg ggagctaatc ccagaaaacc gatcgtagtc cggattgcac tctgcaactc    1260
gagtgcatga agctggaatc gctagtaatc gcggatcagc atgccgcggt gaatacgttc    1320
ccgggtcttg tacacaccgc ccgtcacacc atggagtgg gttttaccag aagtggctag    1380
tctaaccgca aggaggacgg tcaccacggt agga                                 1414
```

<210> SEQ ID NO 4
<211> LENGTH: 1423
<212> TYPE: DNA

<213> ORGANISM: Burkholderia vietnamiensis
<220> FEATURE:
<221> NAME/KEY: misc_feature
<223> OTHER INFORMATION: SGI bacterial isolate SGI-026_G07
<220> FEATURE:
<221> NAME/KEY: misc_feature
<223> OTHER INFORMATION: encodes a 16S ribosomal RNA

<400> SEQUENCE: 4

```
tgccttacac atgcaagtcg aacggcagca cgggtgcttg cacctggtgg cgagtggcga     60
acgggtgagt aatacatcgg aacatgtcct gtagtggggg atagcccggc gaaagccgga    120
ttaataccgc atacgatcta aggatgaaag cgggggacct tcgggcctcg cgctataggg    180
ttggccgatg gctgattagc tagttggtgg ggtaaaggcc taccaaggcg acgatcagta    240
gctggtctga gaggacgacc agccacactg ggactgagac acggcccaga ctcctacggg    300
aggcagcagt ggggaatttt ggacaatggg cgaaagcctg atccagcaat gccgcgtgtg    360
tgaagaaggc cttcgggttg taaagcactt ttgtccggaa agaaatcctt ggctctaata    420
cagtcggggg atgacggtac cggaagaata agcaccggct aactacgtgc cagcagccgc    480
ggtaatacgt agggtgcaag cgttaatcgg aattactggg cgtaaagcgt gcgcaggcgg    540
tttgctaaga ccgatgtgaa atccccgggc tcaacctggg aactgcattg gtgactggca    600
ggctagagta tggcagaggg gggtagaatt ccacgtgtag cagtgaaatg cgtagagatg    660
tggaggaata ccgatggcga aggcagcccc ctgggccaat actgacgctc atgcacgaaa    720
gcgtggggag caaacaggat tagataccct ggtagtccac gccctaaacg atgtcaacta    780
gttgttgggg attcatttcc ttagtaacgt agctaacgcg tgaagttgac cgcctgggga    840
gtacggtcgc aagattaaaa ctcaaaggaa ttgacgggga cccgcacaag cggtggatga    900
tgtggattaa ttcgatgcaa cgcgaaaaac cttacctacc cttgacatgg tcggaagccc    960
gatgagagtt gggcgtgctc gaaagagaac cggcgcacag gtgctgcatg gctgtcgtca   1020
gctcgtgtcg tgagatgttg ggttaagtcc cgcaacgagc gcaacccttg tccttagttg   1080
ctacgcaaga gcactctaag gagactgccg gtgacaaacc ggaggaaggt ggggatgacg   1140
tcaagtcctc atggccctta tgggtagggc ttcacacgtc atacaatggt cggaacagag   1200
ggttgccaac ccgcgagggg gagctaatcc cagaaaaccg atcgtagtcc ggattgcact   1260
ctgcaactcg agtgcatgaa gctggaatcg ctagtaatcg cggatcagca tgccgcggtg   1320
aatacgttcc cgggtcttgt acacaccgcc cgtcacacca tgggagtggg ttttaccaga   1380
agtggctagt ctaaccgcaa ggaggacggt caccacggta gga                      1423
```

<210> SEQ ID NO 5
<211> LENGTH: 1441
<212> TYPE: DNA
<213> ORGANISM: Bacillus pumilus
<220> FEATURE:
<221> NAME/KEY: misc_feature
<223> OTHER INFORMATION: SGI bacterial isolate SGI-034_C09
<220> FEATURE:
<221> NAME/KEY: misc_feature
<223> OTHER INFORMATION: encodes a 16S ribosomal RNA
<220> FEATURE:
<221> NAME/KEY: misc_feature
<222> LOCATION: (605)..(605)
<223> OTHER INFORMATION: n is a, c, g, or t

<400> SEQUENCE: 5

```
gcggcgtgcc taatacatgc aagtcgagcg gacagaaggg agcttgctcc cggatgttag     60
cggcggacgg gtgagtaaca cgtgggtaac ctgcctgtaa gactgggata actccgggaa    120
```

```
accggagcta ataccggata gttccttgaa ccgcatggtt caaggatgaa agacggtttc    180
ggctgtcact tacagatgga cccgcggcgc attagctagt tggtgaggta acggctcacc    240
aaggcgacga tgcgtagccg acctgagagg gtgatcggcc acactgggac tgagacacgg    300
cccagactcc tacgggaggc agcagtaggg aatcttccgc aatggacgaa agtctgacgg    360
agcaacgccg cgtgagtgat gaaggttttc ggatcgtaaa gctctgttgt tagggaagaa    420
caagtgcaag agtaactgct tgcaccttga cggtacctaa ccagaaagcc acggctaact    480
acgtgccagc agccgcggta atacgtaggt ggcaagcgtt gtccggaatt attgggcgta    540
aagggctcgc aggcggtttc ttaagtctga tgtgaaagcc cccggctcaa ccggggaggg    600
tcatnggaaa ctgggaaact tgagtgcaga agaggagagt ggaattccac gtgtagcggt    660
gaaatgcgta gagatgtgga ggaacaccag tggcgaaggc gactctctgg tctgtaactg    720
acgctgagga gcgaaagcgt ggggagcgaa caggattaga taccctggta gtccacgccg    780
taaacgatga gtgctaagtg ttaggggggtt tccgccccctt agtgctgcag ctaacgcatt    840
aagcactccg cctggggagt acggtcgcaa gactgaaact caaaggaatt gacggggggcc    900
cgcacaagcg gtggagcatg tggtttaatt cgaagcaacg cgaagaacct taccaggtct    960
tgacatcctc tgacaaccct agagataggg ctttcccttc ggggacagag tgacaggtgg   1020
tgcatggttg tcgtcagctc gtgtcgtgag atgttgggtt aagtcccgca acgagcgcaa   1080
ccccttgatct tagttgccag cattcagttg ggcactctaa ggtgactgcc ggtgacaaac   1140
cggaggaagg tggggatgac gtcaaatcat catgcccctt atgacctggg ctacacacgt   1200
gctacaatgg acagaacaaa gggctgcgag accgcaaggt ttagccaatc ccacaaatct   1260
gttctcagtt cggatcgcag tctgcaactc gactgcgtga agctggaatc gctagtaatc   1320
gcggatcagc atgccgcggt gaatacgttc ccgggccttg tacacaccgc ccgtcacacc   1380
acgagagttt gcaacacccg aagtcggtga ggtaacctttt atggagccag ccgccgaagg   1440
t                                                                    1441
```

<210> SEQ ID NO 6
<211> LENGTH: 1410
<212> TYPE: DNA
<213> ORGANISM: Herbaspirillum sp.
<220> FEATURE:
<221> NAME/KEY: misc_feature
<223> OTHER INFORMATION: SGI bacterial isolate SGI-034_E10
<220> FEATURE:
<221> NAME/KEY: misc_feature
<223> OTHER INFORMATION: encodes a 16S ribosomal RNA

<400> SEQUENCE: 6

```
tgcaagtcga acggcagca taggagcttg ctcctgatgg cgagtggcga acgggtgagt     60
aatatatcgg aacgtgccct agagtggggg ataactagtc gaaagactag ctaataccgc    120
atacgatcta cggatgaaag tgggggatcg caagaccctca tgctcctgga gcggccgata    180
tctgattagc tagttggtgg ggtaaaagcc taccaaggca acgatcagta gctggtctga    240
gaggacgacc agccacactg ggactgagac acgcccaga ctcctacggg aggcagcagt     300
ggggaatttt ggacaatggg ggcaaccctg atccagcaat gccgcgtgag tgaagaaggc    360
cttcgggttg taaagctctt ttgtcaggga agaaacggta gtagcgaata actattacta    420
atgacggtac ctgaagaata agcaccggct aactacgtgc cagcagccgc ggtaatacgt    480
agggtgcaag cgttaatcgg aattactggg cgtaaagcgt gcgcaggcgg ttgtgtaagt    540
```

```
cagatgtgaa atccccgggc tcaacctggg aattgcattt gagactgcac ggctagagtg      600
tgtcagaggg gggtagaatt ccacgtgtag cagtgaaatg cgtagatatg tggaggaata      660
ccgatggcga aaggcagccc cctgggataa cactgacgct catgcacgaa agcgtgggga      720
gcaaacagga ttagatacnc tggtagtcca cgccctaaac gatgtctact agttgtcggg      780
tcttaattga cttggtaacg cagctaacgc gtgaagtaga ccgcctgggg agtacggtcg      840
caagattaaa actcaaagga attgacgggg acccgcacaa gcggtggatg atgtggatta      900
attcgatgca acgcgaaaaa ccttacctac ccttgacatg gatggaatcc tgaagagatt      960
tgggagtgct cgaaagagaa ccatcacaca ggtgctgcat ggctgtcgtc agctcgtgtc     1020
gtgagatgtt gggttaagtc ccgcaacgag cgcaacccct gtcattagtt gctacgaaag     1080
ggcactctaa tgagactgcc ggtgacaaac cggaggaagg tggggatgac gtcaagtcct     1140
catggccctt atgggtaggg cttcacacgt catacaatgg tacatacaga gggccgccaa     1200
cccgcgaggg ggagctaatc ccagaaagtg tatcgtagtc cggattggag tctgcaactc     1260
gactccatga agttggaatc gctagtaatc gcggatcagc atgtcgcggt gaatacgttc     1320
ccgggtcttg tacacaccgc ccgtcacacc atgggagcgg ttttaccag aagtgggtag      1380 cctaaccgca aggagggcgc tcaccacggt                                       1410
```

<210> SEQ ID NO 7
<211> LENGTH: 1368
<212> TYPE: DNA
<213> ORGANISM: Pedobacter sp.
<220> FEATURE:
<221> NAME/KEY: misc_feature
<223> OTHER INFORMATION: SGI bacterial isolate SGI-041_B03
<220> FEATURE:
<221> NAME/KEY: misc_feature
<223> OTHER INFORMATION: encodes a 16S ribosomal RNA
<220> FEATURE:
<221> NAME/KEY: misc_feature
<222> LOCATION: (529)..(529)
<223> OTHER INFORMATION: n is a, c, g, or t

<400> SEQUENCE: 7

```
gaaagtggcg cacgggtgcg taacgcgtat gcaacctacc ttcatctggg ggatagcccg       60
gagaaatccg gattaatacc gcataaaatc acagtactgc atagtgcaat gatcaaacat      120
ttatgggaag aagatgggca tgcgtgtcat tagctagttg gcggggtaac ggcccaccaa      180
ggcgacgatg actagggat ctgagaggat ggcccccccac actggtactg agacacggac      240
cagactccta cgggaggcag cagtaaggaa tattggtcaa tggaggcaac tctgaaccag      300
ccatgccgcg tgcaggaaga ctgccctatg ggttgtaaac tgcttttatc cgggaataaa      360
cctgagtacg tgtacttagc tgaatgtacc ggaagaataa ggtcggcta actccgtgcc      420 agcagccgcg gtaatacgga ggatccaagc gttatccgga tttattgggt ttaaagggtg      480
cgtaggcggc ctgttaagtc aggggtgaaa gacggtagct caactatcng cagtgccctt      540
gatactgatg ggcttgaatg gactagaggt aggcggaatg agacaagtag cggtgaaatg      600
catagatatg tctcagaaca ccgattgcga aggcagctta ctatggtctt attgacgctg      660
aggcacgaaa gcgtggggat caaacaggat tagatacccct ggtagtccac gccctaaacg      720
atgaacactc gctgttggcg atacacagtc agcggctaag cgaaagcgtt aagtgttcca      780
cctggggagt acgctcgcaa gagtgaaact caaaggaatt gacggggggcc cgcacaagcg      840 gaggagcatg tggtttaatt cgatgatacg cgaggaacct tacccgggct tgaaagttag      900
tgaatcattt agagataaat gagtgagcaa tcacacgaaa ctaggtgctg catggctgtc      960
```

-continued

| | |
|---|---|
| gtcagctcgt gccgtgaggt gttgggttaa gtcccgcaac gagcgcaacc cctatgttta | 1020 |
| gttgccagca cgttatggtg gggactctaa acagactgcc tgtgcaaaca gagaggaagg | 1080 |
| aggggacgac gtcaagtcat catggcccctt acgtccgggg ctacacacgt gctacaatgg | 1140 |
| atggtacaga gggcagctac atagcaatat gatgcgaatc tcacaaagcc attcacagtt | 1200 |
| cggattgggg tctgcaactc gacccccatga agttggattc gctagtaatc gcgtatcagc | 1260 |
| aatgacgcgg tgaatacgtt cccgggcctt gtacacaccg cccgtcaagc catggaagtt | 1320 |
| gggggtacct aaagtatgta accgcaagga gcgtcctagg gtaaaacc | 1368 |

<210> SEQ ID NO 8
<211> LENGTH: 39
<212> TYPE: DNA
<213> ORGANISM: Artificial sequence
<220> FEATURE:
<223> OTHER INFORMATION: PCR primer M13-27F

<400> SEQUENCE: 8

| | |
|---|---|
| tgtaaaacga cggccagtta gagtttgatc ctggctcag | 39 |

<210> SEQ ID NO 9
<211> LENGTH: 37
<212> TYPE: DNA
<213> ORGANISM: Artificial sequence
<220> FEATURE:
<223> OTHER INFORMATION: PCR primer 1492R M13-tailed

<400> SEQUENCE: 9

| | |
|---|---|
| caggaaacag ctatgaccgg ttaccttgtt acgactt | 37 |

<210> SEQ ID NO 10
<211> LENGTH: 1059
<212> TYPE: DNA
<213> ORGANISM: Pantoea agglomerans

<400> SEQUENCE: 10

| | |
|---|---|
| atggctatcg acgaaaacaa acagaaagcg ttggcggcag cactgggcca gatcgaaaaa | 60 |
| cagttcggta aaggctccat catgcgcctg ggtgaagacc gttccatgga cgtggaaact | 120 |
| atctccaccg gttcgctttc cctggatatc gccctcggcg ctggcggtct gccaatgggc | 180 |
| cgtatcgtcg aaatctacgg gcctgaatct tccggtaaaa cgacgctgac cctgcaggtt | 240 |
| atcgccgccg cgcagcgtga aggtaaaacc tgtgccttta tcgatgcaga gcacgcgctg | 300 |
| gatccggtat atgcccgcaa gctgggcgtc gatatcgaca acctgctgtg ctctcagccg | 360 |
| gacaccggcg aacaggcgct tgagatctgt gacgcgctgg cgcgctccgg tgcggtagac | 420 |
| gtgctggtgg tcgactccgt tgcggcgctg acgccgaaag cggaaatcga aggcgagatc | 480 |
| ggcgactctc acatgggcct cgcggcgcgt atgatgagcc aggcaatgcg taagctggcc | 540 |
| ggtaacctga agcagtccaa cacgctgctg atcttcatca accagatccg tatgaaaatt | 600 |
| ggcgtgatgt tcggtaaccc ggaaaccacc accggcggta acgcgctgaa attctacgcc | 660 |
| tccgtgcgtc tggatatccg ccgtatcggt gcggtaaaag atggcgataa cgtcattggt | 720 |
| agcgaaaccc gcgtgaaggt cgtgaagaac aaaatcgccg cgccgttcaa gcaggcggag | 780 |
| ttccagatcc tctacggcga aggcatcaac ttcttcggcg agctggtcga tctgggcgtg | 840 |
| aaagagaagc tgattgaaaa agcgggcgcc tggtatagct acaacggcga caaaattggt | 900 |
| cagggtaaag cgaacgctat ctcctggctg aagagaaacc cggctgcggc gaaagagatc | 960 | gagaagaaag ttcgtgaact gctgctgaac aaccaggatg ccacgccgga cttcgcggtt    1020 gatggtaaaa gcgaagaagc aagcgaacag gatttctga                            1059

<210> SEQ ID NO 11
<211> LENGTH: 352
<212> TYPE: PRT
<213> ORGANISM: Pantoea agglomerans

<400> SEQUENCE: 11

Met Ala Ile Asp Glu Asn Lys Gln Lys Ala Leu Ala Ala Leu Gly
1               5                   10                  15

Gln Ile Glu Lys Gln Phe Gly Lys Gly Ser Ile Met Arg Leu Gly Glu
            20                  25                  30

Asp Arg Ser Met Asp Val Glu Thr Ile Ser Thr Gly Ser Leu Ser Leu
        35                  40                  45

Asp Ile Ala Leu Gly Ala Gly Gly Leu Pro Met Gly Arg Ile Val Glu
    50                  55                  60

Ile Tyr Gly Pro Glu Ser Ser Gly Lys Thr Thr Leu Thr Leu Gln Val
65                  70                  75                  80

Ile Ala Ala Ala Gln Arg Glu Gly Lys Thr Cys Ala Phe Ile Asp Ala
                85                  90                  95

Glu His Ala Leu Asp Pro Val Tyr Ala Arg Lys Leu Gly Val Asp Ile
            100                 105                 110

Asp Asn Leu Leu Cys Ser Gln Pro Asp Thr Gly Glu Gln Ala Leu Glu
        115                 120                 125

Ile Cys Asp Ala Leu Ala Arg Ser Gly Ala Val Asp Val Leu Val Val
    130                 135                 140

Asp Ser Val Ala Ala Leu Thr Pro Lys Ala Glu Ile Glu Gly Glu Ile
145                 150                 155                 160

Gly Asp Ser His Met Gly Leu Ala Ala Arg Met Met Ser Gln Ala Met
                165                 170                 175

Arg Lys Leu Ala Gly Asn Leu Lys Gln Ser Asn Thr Leu Leu Ile Phe
            180                 185                 190

Ile Asn Gln Ile Arg Met Lys Ile Gly Val Met Phe Gly Asn Pro Glu
        195                 200                 205

Thr Thr Thr Gly Gly Asn Ala Leu Lys Phe Tyr Ala Ser Val Arg Leu
    210                 215                 220

Asp Ile Arg Arg Ile Gly Ala Val Lys Asp Gly Asp Asn Val Ile Gly
225                 230                 235                 240

Ser Glu Thr Arg Val Lys Val Val Lys Asn Lys Ile Ala Ala Pro Phe
                245                 250                 255

Lys Gln Ala Glu Phe Gln Ile Leu Tyr Gly Glu Gly Ile Asn Phe Phe
            260                 265                 270

Gly Glu Leu Val Asp Leu Gly Val Lys Glu Lys Leu Ile Glu Lys Ala
        275                 280                 285

Gly Ala Trp Tyr Ser Tyr Asn Gly Asp Lys Ile Gly Gln Gly Lys Ala
    290                 295                 300

Asn Ala Ile Ser Trp Leu Lys Glu Asn Pro Ala Ala Lys Glu Ile
305                 310                 315                 320

Glu Lys Lys Val Arg Glu Leu Leu Leu Asn Asn Gln Asp Ala Thr Pro
                325                 330                 335

Asp Phe Ala Val Asp Gly Lys Ser Glu Glu Ala Ser Glu Gln Asp Phe
            340                 345                 350